(12) United States Patent
Watanabe et al.

(10) Patent No.: US 10,319,917 B2
(45) Date of Patent: Jun. 11, 2019

(54) PHENOXASILINE BASED COMPOUNDS FOR ELECTRONIC APPLICATION

(71) Applicant: UDC Ireland Limited, Dublin (IE)

(72) Inventors: Soichi Watanabe, Seoul Yongsan-gu (KR); Christian Lennartz, Schifferstadt (DE); Gerhard Wagenblast, Wachenheim (DE); Nicolle Langer, Lampertheim (DE); Junji Kido, Yamagata (JP); Hisahiro Sasabe, Yamagata (JP); Masato Kimura, Hyogo (JP)

(73) Assignee: UDC Ireland Limited, Dublin (IE)

( * ) Notice: Subject to any disclaimer, the term of this patent is extended or adjusted under 35 U.S.C. 154(b) by 550 days.

(21) Appl. No.: 14/440,637

(22) PCT Filed: Nov. 6, 2013

(86) PCT No.: PCT/EP2013/073120
§ 371 (c)(1),
(2) Date: May 5, 2015

(87) PCT Pub. No.: WO2014/072320
PCT Pub. Date: May 15, 2014

(65) Prior Publication Data
US 2015/0318501 A1    Nov. 5, 2015

Related U.S. Application Data

(60) Provisional application No. 61/722,809, filed on Nov. 6, 2012.

(30) Foreign Application Priority Data

Nov. 6, 2012 (EP) .................................. 12191408

(51) Int. Cl.
*H01L 51/00* (2006.01)
*C07F 7/08* (2006.01)
*C07F 9/6596* (2006.01)
*H01L 51/52* (2006.01)
*H01L 51/50* (2006.01)

(52) U.S. Cl.
CPC ........ *H01L 51/0069* (2013.01); *C07F 7/0816* (2013.01); *C07F 9/6596* (2013.01); *H01L 51/0058* (2013.01); *H01L 51/0073* (2013.01); *H01L 51/0085* (2013.01); *H01L 51/0094* (2013.01); *H01L 51/0071* (2013.01); *H01L 51/0072* (2013.01); *H01L 51/5012* (2013.01); *H01L 51/5024* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 51/5206* (2013.01); *H01L 51/5221* (2013.01); *H01L 2251/5384* (2013.01); *Y02E 10/549* (2013.01); *Y02P 20/582* (2015.11)

(58) Field of Classification Search
CPC ........................ C07F 7/0816; H01L 51/0094
See application file for complete search history.

(56) References Cited

U.S. PATENT DOCUMENTS

| | | |
|---|---|---|
| 2001/0015432 A1 | 8/2001 | Igarashi |
| 2001/0019782 A1 | 9/2001 | Igarashi et al. |
| 2002/0024293 A1 | 2/2002 | Igarashi et al. |
| 2002/0048689 A1 | 4/2002 | Igarashi et al. |
| 2002/0055014 A1 | 5/2002 | Okada et al. |

(Continued)

FOREIGN PATENT DOCUMENTS

| | | |
|---|---|---|
| EP | 1 191 612 A2 | 3/2002 |
| EP | 1 191 613 A2 | 3/2002 |

(Continued)

OTHER PUBLICATIONS

JP 2003 243178 machine translation (2003).*
International Search Report dated Feb. 28, 2014 in PCT/EP2013/073120.
International Preliminary Report on Patentability and Written Opinion dated May 12, 2015 in PCT/EP2013/073120 (submitting English language translation only).
Kunjanpillai Rajesh, et al., "Homogeneous Hydrogenations of Nitriles Catalyzed by Rhenium Complexes", Advanced Synthesis & Catalysis 353(9), 2011, pp. 1479-1484.

(Continued)

*Primary Examiner* — Kuo Liang Peng
(74) *Attorney, Agent, or Firm* — Riverside Law LLP

(57) ABSTRACT

Organic electronics applications, especially an organic light-emitting diode (OLED), an organic solar cell (organic photovoltaics) or a switching element such as an organic transistor, for example an organic FET (Field Effect Transistor) and an organic TFT (Thin Film Transistor), comprising at least one substituted phenoxasiline derivative, a organic semiconductor layer, a host material, electron/hole/exciton blocking material or electron/hole injection material comprising at least one substituted phenoxasiline derivative, the use of a substituted phenoxasiline derivative in organic electronics applications, an organic light-emitting diode, wherein at least one substituted phenoxasiline derivative is present in the electron/hole/exciton blocking layer, the electron/hole injection layer and/or the light-emitting layer, a light-emitting layer, an electron/hole/exciton blocking layer and an electron/hole injection layer comprising at least one substituted phenoxasiline derivative and a device selected from the group consisting of stationary visual display units, mobile visual display units; illumination units; keyboards; garments; furniture and wallpaper comprising at least one organic light-emitting diode, at least one light-emitting layer, at least one electron/hole/exciton blocking layer and/or at least one electron/hole injection layer according to the present invention.

13 Claims, No Drawings

(56) References Cited

U.S. PATENT DOCUMENTS

| | | |
|---|---|---|
| 2002/0094453 A1 | 7/2002 | Takiguchi et al. |
| 2003/0168970 A1 | 9/2003 | Tominaga et al. |
| 2011/0057559 A1 | 3/2011 | Xia et al. |
| 2011/0253988 A1 | 10/2011 | Molt et al. |

FOREIGN PATENT DOCUMENTS

| | | |
|---|---|---|
| EP | 1 211 257 A2 | 6/2002 |
| EP | 1 341 403 A1 | 9/2003 |
| EP | 1 786 050 A1 | 5/2007 |
| JP | 2003-96072 A | 4/2003 |
| JP | 2003 243178 * | 8/2003 |
| JP | 2003-243178 A | 8/2003 |
| JP | 2004-253298 A | 9/2004 |
| JP | 2006-83167 A | 3/2006 |
| WO | WO 00/70655 A2 | 11/2000 |
| WO | WO 01/41512 A1 | 6/2001 |
| WO | WO 02/02714 A2 | 1/2002 |
| WO | WO 02/15645 A1 | 2/2002 |
| WO | WO 02/60910 A1 | 8/2002 |
| WO | WO 2005/019373 A2 | 3/2005 |
| WO | WO 2005/113704 A2 | 12/2005 |
| WO | WO 2006/056418 A2 | 6/2006 |
| WO | WO 2006/067074 A1 | 6/2006 |
| WO | WO 2006/115301 A1 | 11/2006 |
| WO | WO 2006/121811 A1 | 11/2006 |
| WO | WO 2006/128800 A1 | 12/2006 |
| WO | WO 2007/095118 A2 | 8/2007 |
| WO | WO 2007/115970 A1 | 10/2007 |
| WO | WO 2007/115981 A1 | 10/2007 |
| WO | WO 2008/000727 A1 | 1/2008 |
| WO | WO 2008/034758 A2 | 3/2008 |
| WO | WO 2009/000872 A1 | 12/2008 |
| WO | WO 2009/003919 A1 | 1/2009 |
| WO | WO 2011/073149 A1 | 6/2011 |
| WO | WO 2012/121936 A2 | 9/2012 |

OTHER PUBLICATIONS

M. A. Baldo, et al., "Very high-efficiency green organic light-emitting devices based on electrophosphorescence", Applied Physics Letters, AIP, 1999, vol. 75, No. 1, pp. 4-6.

Mark S. Betson, et al., "Three Groups Good, Four Groups Bad? Atropisomerism in ortho-Substituted Dieryl Ethers", Angewandte Chemie, International Edition, 45(35), 2006, pp. 5803-5807.

N. D. Ghatge et al., "Synthesis and Characterization of Phenoxasilin Containing Polyimides", Journal of Polymer Materials, 1984, vol. 1, No. 4, p. 204-209, Fig. 1, Table 1, Polyimide A to D.

\* cited by examiner

PHENOXASILINE BASED COMPOUNDS FOR ELECTRONIC APPLICATION

The present invention relates to organic electronics applications, especially an organic light-emitting diode (OLED), to an organic solar cell (organic photovoltaics) or a switching element such as an organic transistor, for example an organic FET (Field Effect Transistor) and an organic TFT (Thin Film Transistor), comprising at least one substituted phenoxasiline derivative, to a organic semiconductor layer, a host material, electron/hole/exciton blocking material or electron/hole injection material comprising at least one substituted phenoxasiline derivative, the use of a substituted phenoxasiline derivative in organic electronics applications, an organic light-emitting diode, wherein at least one substituted phenoxasiline derivative is present in the electron/hole/exciton blocking layer, the electron/hole injection layer and/or the light-emitting layer, a light-emitting layer, an electron/hole/exciton blocking layer and an electron/hole injection layer comprising at least one substituted phenoxasiline derivative and to a device selected from the group consisting of stationary visual display units such as visual display units of computers, televisions, visual display units in printers, kitchen appliances and advertising panels, illuminations, information panels, and mobile visual display units such as visual display units in smartphones, cellphones, laptops, digital cameras, MP3 players, vehicles and destination displays on buses and trains; illumination units; keyboards; garments; furniture and wallpaper comprising at least one organic light-emitting diode, at least one light-emitting layer, at least one electron/hole/exciton blocking layer and/or at least one electron/hole injection layer according to the present invention.

Organic electronics is a subfield of electronics which uses electronic circuits which comprise polymers or smaller organic compounds. Fields of use of organic electronics are the use of polymers or smaller organic compounds in organic light-emitting diodes (OLEDs), use in organic solar cells (organic photovoltaics) and in switching elements such as organic transistors, for example organic FETs and organic TFTs.

The use of suitable novel organic materials thus allows various new types of components based on organic electronics to be provided, such as displays, sensors, transistors, data stores or photovoltaic cells. This makes possible the development of new applications which are thin, light, flexible and producible at low cost.

A preferred field of use according to the present application is the use of relatively small organic compounds in organic light-emitting diodes.

Organic light-emitting diodes (OLEDs) exploit the property of materials of emitting light when they are excited by electrical excitation. OLEDs are of particular interest as an alternative to cathode ray tubes and liquid-crystal displays for producing flat visual display units. Owing to the very compact design and the intrinsically low power consumption, the devices comprising OLEDs are suitable especially for mobile applications, for example for applications in smartphones, cellphones, laptops, etc., and for illumination.

The basic principles of the way in which OLEDs work and suitable structures (layers) of OLEDs are specified, for example, in WO 2005/113704 and the literature cited therein.

The light-emitting materials (emitters) used may, as well as fluorescent materials (fluorescent emitters), be phosphorescent materials (phosphorescent emitters). The phosphorescent emitters are typically organometallic complexes which, in contrast to the fluorescence emitters which exhibit singlet emission, exhibit triplet emission (M. A. Baldow et al., Appl. Phys. Lett. 1999, 75, 4 to 6). For quantum-mechanical reasons, when the phosphorescent emitters are used, up to four times the quantum efficiency, energy efficiency and power efficiency is possible.

Of particular interest are organic light-emitting diodes with a low operational voltage, high efficiency, high efficacy, high resistance to thermal stress and long operational lifetime.

In order to implement the aforementioned properties in practice, it is not only necessary to provide suitable emitter materials, but the other components of the OLED (complementary materials) must also be balanced to one another in suitable device compositions. Such device compositions may, for example, comprise specific host (matrix) materials in which the actual light emitter is present in distributed form. In addition, the compositions may comprise blocker materials, it being possible for hole blockers, exciton blockers and/or electron blockers to be present in the device compositions. Additionally or alternatively, the device compositions may further comprise hole injection materials and/or electron injection materials and/or charge transport materials such as hole transport materials and/or electron transport materials. The selection of the aforementioned materials which are used in combination with the actual light emitter has a significant influence on parameters including the efficiency and the lifetime, and the use and operating voltages, of the OLEDs.

The prior art proposes numerous different materials for use in the different layers of OLEDs.

The use of phenoxasilines in organic electronics applications has only been described in a few prior art references in general terms.

JP-A 2003096072 and EP 1 341 403 A1 concern the use of spiro compounds of the following formula in OLEDs:

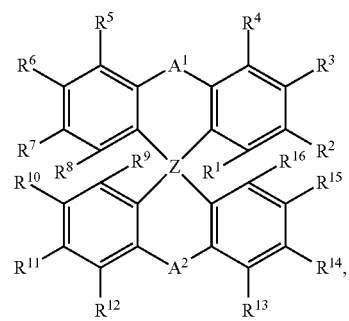

wherein Z is C or Si, and A1 and A2 are each selected from single bonds, substituted or unsubstituted alkyl chains, ether chains, thioether chains, ketone chains and substituted or unsubstituted amino chains.

According to JP-A 2003096072 the spiro compound is used as a light emitting substance in OLEDs.

JP-A 2004253298 relates to an uniform white light-emitting organic electroluminescent element with high efficiency and a long life. The OLED according to JP-A 2004253298 comprises a fluorescent compound selected from numerous different compounds. The fluorescent compound may be for example a compound of the following formula

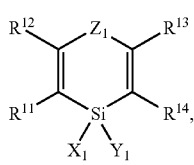

wherein $Z_1$ is selected from $CR^{15}R^{16}$, O, S and $SiR^{17}R^{18}$.

JP-A 2003243178 concerns an OLED with high luminescence brightness and durability. The OLED comprises at least one compound of the following formula

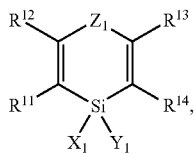

wherein $Z_1$ is selected from $CR^{15}R^{16}$, O, S and $SiR^{17}R^{18}$.

It is an object of the present application, with respect to the prior art, to provide novel device compositions for applications in organic electronics applications such as OLEDs, organic solar cells and switching elements, especially for OLEDs, which comprise materials for improvement of the performance of OLEDs, organic solar cells and switching elements, especially of OLEDs.

The materials suitable for the novel device compositions should have good availability and stability and—in the case of OLEDs—result in high efficiencies and long lifetimes and low driving voltages in OLEDs, in combination with the emitters used in the OLEDs. More particularly, it is an object of the present application to provide materials which result in long lifetimes in OLEDs, organic solar cells and switching elements, especially in OLEDs. In addition, OLEDs with high efficiency and color purity are to be provided.

This object is achieved by the provision of organic electronics applications, especially an organic light-emitting diode (OLED), an organic solar cell or a switching element, preferably an organic light-emitting diode (OLED), comprising at least one compound of the formula (I)

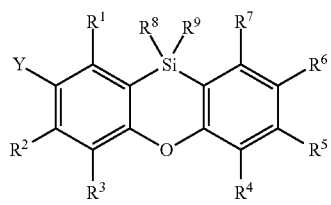

(I)

in which $R^1$, $R^2$, $R^3$, $R^4$, $R^5$, $R^6$ and $R^7$
are each independently hydrogen, $C_1$-$C_{20}$-alkyl, $C_3$-$C_{20}$-cycloalkyl, heterocycloalkyl having 3 to 20 ring atoms, $C_6$-$C_{30}$-aryl, heteroaryl having 5 to 30 ring atoms or a substituent with donor or acceptor action selected from the group consisting of $C_1$-$C_{20}$-alkoxy, $C_6$-$C_{30}$-aryloxy, $C_1$-$C_{20}$-alkylthio, $C_6$-$C_{30}$-arylthio, $SiR^{10}R^{11}R^{12}$, halogen radicals, halogenated $C_1$-$C_{20}$-alkyl radicals, carbonyl (—CO($R^{10}$)), carbonylthio (—C=O($SR^{10}$)), carbonyloxy (—C=O($OR^{10}$)), oxycarbonyl (—OC=O($R^{10}$)), thiocarbonyl (—SC=O($R^{10}$)), amino (—$NR^{10}R^{11}$), OH, pseudohalogen radicals, amido (—C=O($NR^{10}$)), —$NR^{10}$C=O($R^{11}$), phosphonate (—P(O)($OR^{10}$)$_2$), phosphate (—OP(O)($OR^{10}$)$_2$), phosphine (—$PR^{10}R^{11}$), phosphine oxide (—P(O)$R^{10}_2$), sulfate (—OS(O)$_2$$OR^{10}$), sulfoxide (—S(O)$R^{10}$), sulfonate (—S(O)$_2$$OR^{10}$), sulfonyl (—S(O)$_2$$R^{10}$), sulfonamide (—S(O)$_2$$NR^{10}R^{11}$), $NO_2$, boronic esters (—OB($OR^{10}$)$_2$), imino (—C=$NR^{10}R^{11}$), borane radicals, stannane radicals, hydrazine radicals, hydrazone radicals, oxime radicals, nitroso groups, diazo groups, vinyl groups, sulfoximines, alanes, germanes, boroximes and borazines;

or two adjacent $R^1$, $R^2$, $R^3$, $R^4$, $R^5$, $R^6$ or $R^7$ radicals, in each case together with the carbon atoms to which they are bonded, form a ring having a total of 3 to 12 atoms, where the ring may be saturated or mono- or polyunsaturated and, as well as carbon atoms, may have one or more heteroatoms selected from N, O and P, where the ring may be unsubstituted or mono- or polysubstituted and/or may be fused to further 3- to 12-membered rings;

$R^8$ and $R^9$
are each independently $C_1$-$C_{20}$-alkyl, $C_3$-$C_{20}$-cycloalkyl, heterocycloalkyl having 3 to 20 ring atoms, $C_6$-$C_{30}$-aryl or heteroaryl having 5 to 30 ring atoms;

$R^{10}$, $R^{11}$, $R^{12}$
are each independently $C_1$-$C_{20}$-alkyl, $C_3$-$C_{20}$-cycloalkyl, heterocycloalkyl having 3 to 20 ring atoms, $C_6$-$C_{30}$-aryl, heteroaryl having 5 to 30 ring atoms, —O—Si($C_1$-$C_{20}$-alkyl)$_3$, —O—Si($C_6$-$C_{30}$-aryl)$_3$, $C_1$-$C_{20}$-alkoxy or $C_6$-$C_{30}$-aryloxy;

or two adjacent $R^{10}$ and $R^{11}$, $R^{10}$ and $R^{12}$ or $R^{11}$ and $R^{12}$ radicals, together with the atom to which they are bonded, form a ring having a total of 3 to 12 atoms, where the ring may be saturated or mono- or polyunsaturated and, as well as the atom to which the $R^{10}$, $R^{11}$ or $R^{12}$ radicals are bonded, may have exclusively carbon atoms or one or more further heteroatoms selected from N, O and P, where the ring may be unsubstituted or mono- or polysubstituted and/or may be fused to further 3- to 12-membered rings;

Y $C_2$-$C_{20}$-alkyl, $C_3$-$C_{20}$-cycloalkyl, heterocycloalkyl having 3 to 20 ring atoms, $C_6$-$C_{30}$-aryl, heteroaryl having 5 to 30 ring atoms or a substituent with donor or acceptor action selected from the group consisting of $C_1$-$C_{20}$-alkoxy, $C_6$-$C_{30}$-aryloxy, $C_1$-$C_{20}$-alkylthio, $C_6$-$C_{30}$-arylthio, $SiR^{10}R^{11}R^{12}$, halogen radicals, halogenated $C_1$-$C_{20}$-alkyl radicals, carbonyl (—CO($R^{10}$)), carbonylthio (—C=O($SR^{10}$)), carbonyloxy (—C=O($OR^{10}$)), oxycarbonyl (—OC=O($R^{10}$)), thiocarbonyl (—SC=O($R^{10}$)), amino (—$NR^{10}R^{11}$), OH, pseudohalogen radicals, amido (—C=O($NR^{10}$)), —$NR^{10}$C=O($R^{11}$), phosphonate (—P(O)($OR^{10}$)$_2$), phosphate (—OP(O)($OR^{10}$)$_2$), phosphine (—$PR^{10}R^{11}$), phosphine oxide (—P(O)$R^{10}_2$), sulfate (—OS(O)$_2$$OR^{10}$), sulfoxide (—S(O)$R^{10}$), sulfonate (—S(O)$_2$$OR^{10}$), sulfonyl (—S(O)$_2$$R^{10}$), sulfonamide (—S(O)$_2$$NR^{10}R^{11}$), $NO_2$, boronic esters (—OB($OR^{10}$)$_2$), imino (—C=$NR^{10}R^{11}$), borane radicals, stannane radicals, hydrazine radicals, hydrazone radicals, oxime radicals, nitroso groups, diazo groups, vinyl groups, sulfoximines, alanes, germanes, boroximes and borazines; preferably heteroaryl having 5 to 30 ring atoms selected from the group consisting of pyrrolyl, furanyl, thienyl, benzoanellated ring systems of pyrrolyl, furanyl, thienyl, for example benzofuranyl, benzothienyl, indolyl, isoindolyl, isoindolizinyl, carbazolyl, azacarbazolyl, diazacarbazolyl, dibenzofuryl, dibenzothienyl, pyridyl, pyrimidyl, pyrazolyl, imidazolyl, thiazolyl, oxazolyl, triazoly and phenanthrolinyl; or $SiR^{10}R^{11}R^{12}$.

In the context of the present application "organic electronics applications" means "organic electronics devices"

By virtue of the use of the phenoxasiline derivatives of the formula (I) substituted by at least one substituent Y, organic electronics applications, especially OLEDs, organic solar cells and switching elements, preferably OLEDs, with a long lifetime a low driving voltage and a high efficiency are obtained. In addition, in OLEDs having the phenoxasiline derivatives of the formula (I) used in accordance with the invention, problematic aggregation and exciplex formation, which result in loss of efficiency and color purity, are avoided. It is thus possible in accordance with the invention to provide highly effective and pure-color OLEDs with long lifetime or organic solar cells and switching elements with long lifetime.

It has been found that the phenoxasiline derivatives of the formula (I) are particularly suitable for use in applications in which charge carrier transporting and injection performance is required, especially for use in organic electronics applications, for example selected from switching elements such as organic transistors, e.g. organic FETs (field-effect transistors) and organic TFTs (thin-film transistors), organic solar cells and organic light-emitting diodes (OLEDs), the phenoxasiline derivatives of the formula (I) in OLEDs being particularly suitable for use as host (matrix) material, preferably in a light-emitting layer, and/or as electron/hole/exciton transport material and/or as electron/hole/exciton blocking material and/or as electron/hole/exciton injection material, especially in combination with a phosphorescence emitter or as an organic semiconductor layer.

Under the terms "electron/hole/exciton transport material" or layer, "electron/hole/exciton blocking material" or layer and "electron/hole/exciton injection material" or layer it is to be understood "electron/exciton transport material" or layer or "hole/exciton transport material" or layer; "electron/exciton blocking material" or layer or "hole/exciton blocking material" or layer; respectively "electron/exciton injection material" or layer or "hole/exciton injection material" or layer.

In the case of use of the phenoxasiline derivatives of the formula (I) in OLEDs, OLEDs are obtained which have good efficiencies and a long lifetime, and which can be operated especially at a low use and operating voltage. In addition, the OLEDs have a high color purity. The phenoxasiline derivatives of the formula (I) are especially suitable for use as host (matrix) and/or electron/hole/exciton transport material, electron/hole/exciton blocking materials and/or electron/hole injection materials for blue, green and red, especially blue emitters, for example light blue or deep blue emitters, these being especially phosphorescence emitters. The high triplet energy level of the phenoxasiline derivatives of formula (I) sufficiently confines light as well as deep blue excitons within the emissive layer. Therefore highly efficient blue light emitting OLEDs are obtained by employing the phenoxasiline derivatives of formula (I). In addition, the phenoxasiline derivatives of the formula (I) can be used as host (matrix) and/or electron/hole/exciton transport material, electron/hole/exciton blocking materials and/or electron/hole injection materials in organic electronics applications selected from switching elements and organic solar cells.

The phenoxasiline derivatives of the formula (I) used in accordance with the invention can preferably be used as host (matrix) materials in the light-emitting layer E or any other layer of an OLED, preferably as host (matrix) materials in the light-emitting layer E, as an electron/hole/exciton transport material, as an electron/hole/exciton blocker or as electron/hole/exciton injection materials. Corresponding layers of OLEDs are known to those skilled in the art and are specified, for example, in WO 2005/113704 or WO 2005/019373. Preference is given to using the phenoxasiline derivatives of the formula (I) used in accordance with the invention as host (matrix) materials or electron/hole/exciton transport materials.

$C_1$-$C_{20}$-alkyl is understood to mean substituted or unsubstituted alkyl radicals having from 1 to 20 carbon atoms. Preference is given to $C_1$- to $C_{10}$-alkyl radicals, particular preference to $C_1$- to $C_6$-alkyl radicals. The alkyl radicals may be either straight-chain or branched or cyclic, where the alkyl radicals in the case of cyclic alkyl radicals have at least 3 carbon atoms. In addition, the alkyl radicals may be substituted by one or more substituents selected from the group consisting of $C_1$-$C_{20}$-alkoxy, halogen, preferably F, and $C_6$-$C_{30}$-aryl which may in turn be substituted or unsubstituted. Suitable aryl substituents and suitable alkoxy and halogen substituents are specified below. Examples of suitable alkyl groups are methyl, ethyl, propyl, butyl, pentyl, hexyl, heptyl and octyl, and also derivatives of the alkyl groups mentioned substituted by $C_6$-$C_{30}$-aryl, $C_1$-$C_{20}$-alkoxy and/or halogen, especially F, for example $CF_3$. This includes both the n-isomers of the radicals mentioned and branched isomers such as isopropyl, isobutyl, isopentyl, sec-butyl, tert-butyl, neopentyl, 3,3-dimethylbutyl, 3-ethylhexyl, etc. Preferred alkyl groups are methyl, ethyl, tert-butyl and $CF_3$.

Examples of suitable cyclic alkyl groups ($C_3$-$C_{20}$-cycloalkyl), which may likewise be unsubstituted or substituted by the above radicals specified for the alkyl groups, are cyclopropyl, cyclobutyl, cyclopentyl, cyclohexyl, cycloheptyl, cyclooctyl, cyclononyl and cyclodecyl. These may optionally also be polycyclic ring systems, such as fluorenyl, decalinyl, norbornyl, bornanyl or adamantyl.

Heterocycloalkyl with 3 to 20 ring atoms is understood to mean substituted or unsubstituted heterocycloalkyl having 3 to 20 ring atoms, which derive from the aforementioned cycloalkyl, wherein at least one atom of the ring atoms in the cycloalkyl base skeleton is replaced by a heteroatom. Preferred heteroatoms are N, O, Si and S. Preferred heterocycloalkyl radicals have a base skeleton selected from systems such as pyrrolidinyl, tetrahydofuryl, tetrahydrothienyl, piperidyl, tetrahydropyranyl, tetrahydrothiopyranyl, piperazinyl, morpholinyl, azasilinyl, oxasilinyl. These may optionally also be fused to form polycyclic ring sytems, e.g. fused to one or two sixmembered aromatic radicals. Suitable fused systems are for example phenoxasilinyl or phenazasilinyl. The base skeleton may be substituted at one, more than one or all substitutable positions, suitable substituents being the same specified below under the definition of $C_6$-$C_{30}$-aryl. However, the heterocycloalkyl radicals are preferably unsubstituted or substituted by one of the substituents mentioned before.

Preferred phenoxasilinyl groups are groups of the formula (I')

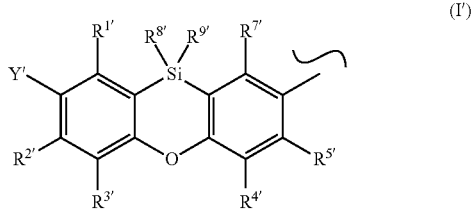

(I')

wherein the substituents Y', R$^{1'}$, R$^{2'}$, R$^{3'}$, R$^{4'}$, R$^{5'}$, R$^{7'}$ R$^{8'}$ and R$^{9'}$ have independently the same meanings as the substituents Y, R$^1$, R$^2$, R$^3$, R$^4$, R$^5$, R$^7$, R$^8$ and R$^9$ in the phenoxasiline derivatives of formula (I).

The symbol ~ means that there is a binding site at the position marked with ~.

Suitable C$_1$-C$_{20}$-alkoxy and C$_1$-C$_{20}$-alkylthio groups derive correspondingly from the aforementioned C$_1$-C$_{20}$-alkyl radicals. Examples here include OCH$_3$, OC$_2$H$_5$, OC$_3$H$_7$, OC$_4$H$_9$ and OC$_8$H$_{17}$, and also SCH$_3$, SC$_2$H$_5$, SC$_3$H$_7$, SC$_4$H$_9$ and SC$_8$H$_{17}$. C$_3$H$_7$, C$_4$H$_9$ and C$_8$H$_{17}$ include both the n-isomers and branched isomers such as iso-propyl, isobutyl, sec-butyl, tert-butyl and 2-ethylhexyl. Particularly preferred alkoxy or alkylthio groups are methoxy, ethoxy, n-octyloxy, 2-ethylhexyloxy and SCH$_3$.

Suitable halogen radicals or halogen substituents in the context of the present application are fluorine, chlorine, bromine and iodine, preferably fluorine, chlorine and bromine, more preferably fluorine and chlorine, most preferably fluorine.

Suitable pseudohalogen radicals in the context of the present application are CN, SCN, OCN, N$_3$ and SeCN, preference being given to CN and SCN. Very particular preference is given to CN.

In the present invention, C$_6$-C$_{30}$-aryl refers to radicals which are derived from monocyclic, bicyclic or tricyclic aromatics which do not comprise any ring heteroatoms. When the system is not a monocyclic system, the saturated form (perhydro form) or the partly unsaturated form (for example the dihydro form or tetrahydro form) are also possible for the second ring in the case of the designation "aryl", provided that the particular forms are known and stable. In other words, the term "aryl" in the present invention also comprises, for example, bicyclic or tricyclic radicals in which either both or all three radicals are aromatic, and also bicyclic or tricyclic radicals in which only one ring is aromatic, and also tricyclic radicals in which two rings are aromatic. Examples of aryl are: phenyl, naphthyl, indanyl, 1,2-dihydronaphthenyl, 1,4-dihydronaphthenyl, indenyl, anthracenyl, phenanthrenyl or 1,2,3,4-tetrahydronaphthyl. Particular preference is given to C$_6$-C$_{10}$-aryl radicals, for example phenyl or naphthyl, very particular preference to C$_6$-aryl radicals, for example phenyl.

The C$_6$-C$_{30}$-aryl radicals may be unsubstituted or substituted by one or more further radicals. Suitable further radicals are selected from the group consisting of C$_1$-C$_{20}$-alkyl, C$_3$-C$_{20}$-cycloalkyl, heterocycloalkyl having 3 to 20 ring atoms, C$_6$-C$_{30}$-aryl or substituents with donor or acceptor action, suitable substituents with donor or acceptor action being specified below. The C$_6$-C$_{30}$-aryl radicals are preferably unsubstituted or substituted by one or more C$_1$-C$_{20}$-alkoxy groups, CN, CF$_3$, F or amino groups (NR$^{10}$R$^{11}$, where suitable R$^{10}$ and R$^{11}$ radicals are specified above). Most preferably is unsubstituted phenyl or phenyl substituted with a phenoxasilinyl group, whereby a preferred phenoxasilinyl group is a phenoxasilinyl group of formula (I') as mentioned before.

Suitable C$_6$-C$_{30}$-aryloxy, C$_6$-C$_{30}$-alkylthio radicals derive correspondingly from the aforementioned C$_6$-C$_{30}$-aryl radicals. Particular preference is given to phenoxy and phenylthio. Heteroaryl having from 5 to 30 ring atoms is understood to mean unsubstituted or substituted monocyclic, bicyclic or tricyclic heteroaromatics which derive from the aforementioned aryl, in which at least one carbon atom in the aryl base skeleton has been replaced by a heteroatom. Preferred heteroatoms are N, O, Si and S. The heteroaryl radicals more preferably have from 5 to 13 ring atoms. Especially preferably, the base skeleton of the heteroaryl radicals is selected from systems such as pyridine and five-membered heteroaromatics such as thiophene, pyrrole, imidazole, silole or furan. These base skeletons may optionally be fused to one or two sixmembered aromatic radicals. Suitable fused heteroaromatics are carbazolyl, azacarbazolyl, diazacarbazolyl, benzimidazolyl, benzofuryl, dibenzofuryl or dibenzothiophenyl. The base skeleton may be substituted at one, more than one or all substitutable positions, suitable substituents being the same as have already been specified under the definition of C$_6$-C$_{30}$-aryl. However, the heteroaryl radicals are preferably unsubstituted or substituted with a phenoxasilinyl group, whereby a preferred phenoxasilinyl group is a phenoxasilinyl group of formula (I') as mentioned before. Suitable heteroaryl radicals are, for example, pyridin-2-yl, pyridin-3-yl, pyridin-4-yl, thiophen-2-yl, thiophen-3-yl, pyrrol-2-yl, pyrrol-3-yl, furan-2-yl, furan-3-yl and imidazol-2-yl, and also the corresponding benzofused radicals, especially carbazolyl, azacarbazolyl, diazacarbazolyl, benzimidazolyl, benzofuryl, dibenzofuryl or dibenzothiophenyl. Further preferred heteroaryl radicals are mentioned below in the discussion of the specific radicals of the compound of formula (I).

In the context of the present application, groups with donor or acceptor action are understood to mean the following groups:
C$_1$-C$_{20}$-alkoxy, C$_6$-C$_{30}$-aryloxy, C$_1$-C$_{20}$-alkylthio, C$_6$-C$_{30}$-arylthio, SiR$^{10}$R$^{11}$R$^{12}$, halogen radicals, halogenated C$_1$-C$_{20}$-alkyl radicals, carbonyl (—CO(R$^{10}$)), carbonylthio (—C=O(SR$^{10}$)), carbonyloxy (—C=O(OR$^{10}$)), oxycarbonyl (—OC=O(R$^{10}$)), thiocarbonyl (—SC=O(R$^{10}$)), amino (—NR$^{10}$R$^{11}$), OH, pseudohalogen radicals, amido (—C=O (NR$^{10}$)), —NR$^{10}$C=O(R$^{11}$), phosphonate (—P(O)-(OR$^{10}$)$_2$), phosphate (—OP(O)(OR$^{10}$)$_2$), phosphine (—PR$^{10}$R$^{11}$), phosphine oxide (—P(O)R$^{10}$$_2$), sulfate (—OS (O)$_2$OR$^{10}$), sulfoxide (—S(O)R$^{10}$), sulfonate (—S(O)$_2$OR$^{10}$), sulfonyl (—S(O)$_2$R$^{10}$), sulfonamide (—S (O)$_2$NR$^{10}$R$^{11}$), NO$_2$, boronic esters (—OB(OR$^{10}$)$_2$), imino (—C=NR$^{10}$R$^{11}$), borane radicals, stannane radicals, hydrazine radicals, hydrazone radicals, oxime radicals, nitroso groups, diazo groups, vinyl groups, and boronic acid groups, sulfoximines, alanes, germanes, boroximes and borazines.

Preferred substituents with donor or acceptor action are selected from the group consisting of:
C$_1$- to C$_{20}$-alkoxy, preferably C$_1$-C$_6$-alkoxy, more preferably ethoxy or methoxy; C$_6$-C$_{30}$-aryloxy, preferably C$_6$-C$_{10}$-aryloxy, more preferably phenyloxy; SiR$^{10}$R$^{11}$R$^{12}$ where R$^{10}$, R$^{11}$ and R$^{12}$ are preferably each independently substituted or unsubstituted alkyl or substituted or unsubstituted phenyl; more preferably, at least one of the R$^{10}$, R$^{11}$ or R$^{12}$ radicals is substituted or unsubstituted phenyl; most preferably, at least one of the R$^{10}$, R$^{11}$ or R$^{12}$ radicals is substituted phenyl, where suitable substituents have been specified above; halogen radicals, preferably F, Cl, Br, more preferably F or Cl, most preferably F, halogenated $C_1$-$C_{20}$-alkyl radicals, preferably halogenated $C_1$-$C_6$-alkyl radicals, most preferably fluorinated $C_1$-$C_6$-alkyl radicals, e.g. $CF_3$, $CH_2F$, $CHF_2$ or $C_2F_5$; amino, preferably dimethylamino, diethylamino or diphenylamino; OH, pseudohalogen radicals, preferably CN, SCN or OCN, more preferably CN, —C(O)O$C_1$-$C_4$-alkyl, preferably —C(O)OMe, P(O)$R_2$, preferably P(O)$Ph_2$ or $SO_2R^2$, preferably $SO_2Ph$.

Very particularly preferred substituents with donor or acceptor action are selected from the group consisting of methoxy, phenyloxy, halogenated $C_1$-$C_4$-alkyl, preferably $CF_3$, $CH_2F$, $CHF_2$, $C_2F_5$, halogen, preferably F, CN, $SiR^{10}R^{11}R^{12}$, diphenylamino, —C(O)O$C_1$-$C_4$-alkyl, preferably —C(O)OMe, P(O)$Ph_2$, $SO_2Ph$.

The aforementioned groups with donor or acceptor action are not intended to rule out the possibility that further aforementioned radicals and groups may also have donor or acceptor action.

For example, the aforementioned heteroaryl radicals are likewise groups with donor or acceptor action, and the $C_1$-$C_{20}$-alkyl radicals are groups with donor action.

The $R^{10}$, $R^{11}$ and $R^{12}$ radicals mentioned in the aforementioned groups with donor or acceptor action each have the definitions which have already been mentioned above and are mentioned below.

Preferably, $R^{10}$, $R^{11}$, $R^{12}$ are each independently $C_6$-$C_{30}$-aryl, more preferably phenyl, which is even more preferably unsubstituted.

The radical Y in the phenoxasiline derivatives of the formula (I) is $C_2$-$C_{20}$-alkyl, $C_3$-$C_{20}$-cycloalkyl, heterocycloalkyl having 3 to 20 ring atoms, $C_6$-$C_{30}$-aryl, heteroaryl having 5 to 30 ring atoms or a substituent with donor or acceptor action selected from the group consisting of $C_1$-$C_{20}$-alkoxy, $C_6$-$C_{30}$-aryloxy, $C_1$-$C_{20}$-alkylthio, $C_6$-$C_{30}$-arylthio, $SiR^{10}R^{11}R^{12}$, halogen radicals, halogenated $C_1$-$C_{20}$-alkyl radicals, carbonyl (—CO($R^{10}$)), carbonylthio (—C=O(S$R^{10}$)), carbonyloxy (—C=O(O$R^{10}$)), oxycarbonyl (—OC=O($R^{10}$)), thiocarbonyl (—SC=O($R^{10}$)), amino (—N$R^{10}R^{11}$), OH, pseudohalogen radicals, amido (—C=O(N$R^{10}$)), —N$R^{10}$C=O($R^{11}$), phosphonate (—P(O)(O$R^{10}$)$_2$), phosphate (—OP(O)(O$R^{10}$)$_2$), phosphine (—P$R^{10}R^{11}$), phosphine oxide (—P(O)$R^{10}_2$), sulfate (—OS(O)$_2$O$R^{10}$), sulfoxide (—S(O)$R^{10}$), sulfonate (—S(O)$_2$O$R^{10}$), sulfonyl (—S(O)$_2R^{10}$), sulfonamide (—S(O)$_2$N$R^{10}R^{11}$), $NO_2$, boronic esters (—OB(O$R^{10}$)$_2$), imino (—C=N$R^{10}R^{11}$), borane radicals, stannane radicals, hydrazine radicals, hydrazone radicals, oxime radicals, nitroso groups, diazo groups, vinyl groups, sulfoximines, alanes, germanes, boroximes and borazines; and $R^{10}$, $R^{11}$ and $R^{12}$ are each independently $C_1$-$C_{20}$-alkyl, $C_3$-$C_{20}$-cycloalkyl, heterocycloalkyl having 3 to 20 ring atoms, $C_6$-$C_{30}$-aryl, heteroaryl having 5 to 30 ring atoms, —O—Si($C_1$-$C_{20}$-alkyl)$_3$, —O—Si($C_6$-$C_{30}$-aryl)$_3$, $C_1$-$C_{20}$-alkoxy or $C_6$-$C_{30}$-aryloxy; preferably $C_6$-$C_{30}$-aryl, more preferably phenyl;

or two adjacent $R^{10}$ and $R^{11}$, $R^{10}$ and $R^{12}$ or $R^{11}$ and $R^{12}$ radicals, together with the atom to which they are bonded, form a ring having a total of 3 to 12 atoms, where the ring may be saturated or mono- or polyunsaturated and, as well as the atom to which the $R^{10}$, $R^{11}$ or $R^{12}$ radicals are bonded, may have exclusively carbon atoms or one or more further heteroatoms selected from N, O and P, where the ring may be unsubstituted or mono- or polysubstituted and/or may be fused to further 3- to 12-membered rings.

Preferably, Y is heteroaryl having 5 to 30 ring atoms selected from the group consisting of pyrrolyl, furanyl, thienyl, benzoanellated ring systems of pyrrolyl, furanyl, thienyl, for example benzofuranyl, benzothienyl, indolyl, isoindolyl, isoindolizinyl, carbazolyl, azacarbazolyl, diazacarbazolyl, dibenzofuryl, dibenzothienyl, pyridyl, pyrimidyl, pyrazolyl, imidazolyl, thiazolyl, oxazolyl, triazoly and phenanthrolinyl; or $SiR^{10}R^{11}R^{12}$; and $R^{10}$, $R^{11}$ and $R^{12}$ are each independently $C_6$-$C_{30}$-aryl, preferably phenyl.

More preferably, Y is selected from the group consisting of unsubstituted or substituted pyrrolyl, furanyl, thienyl, benzofuranyl, benzothienyl, indolyl, isoindolyl, isoindolizinyl, carbazolyl, azacarbazolyl, diazacarbazolyl, dibenzofuryl, dibenzothienyl and $SiPh_3$.

Even more preferably, Y is selected from the group consisting of

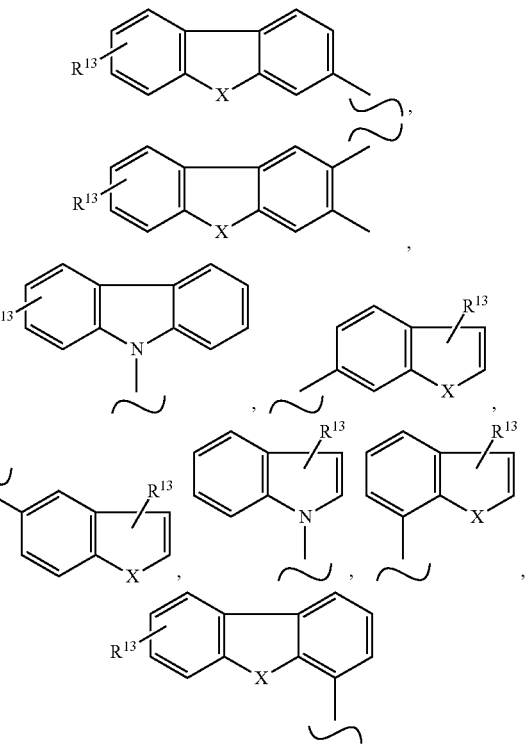

and $SiPh_3$,
wherein
X is $NR^{10}$, O or S,
$R^{10}$ is $C_1$-$C_{20}$-alkyl, $C_6$-$C_{30}$-aryl, heteroaryl having 5 to 30 ring atoms, —O—Si($C_1$-$C_{20}$-alkyl)$_3$, —O—Si($C_6$-$C_{30}$-aryl)$_3$, $C_1$-$C_{20}$-alkoxy or $C_6$-$C_{30}$-aryloxy; preferably $C_6$-$C_{30}$-aryl, more preferably phenyl, and
$R^{13}$ is H or phenoxasilinyl of formula (I'), preferably H.

The symbol ~ means that there is a binding site at the position marked with ~.

Even more preferably, Y is selected from the group consisting of

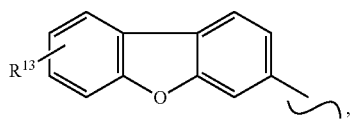

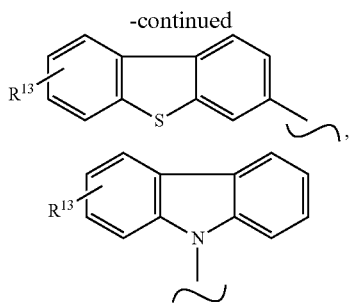

and SiPh₃,
wherein
R¹³ is H or phenoxasilinyl of formula (I'), preferably H.

The symbol ~ means that there is a binding site at the position marked with ~.

R⁸ and R⁹ in the phenoxasilines of formula (I) are each independently $C_1$-$C_{20}$-alkyl, $C_6$-$C_{30}$-aryl, heteroaryl having 5 to 30 ring atoms.

Preferably, R⁸ and R⁹ are each independently $C_6$-$C_{30}$-aryl or heteroaryl having 5 to 30 ring atoms.

More preferably, R⁸ and R⁹ are each independently phenyl, which is most preferably unsubstituted, dibenzofuranyl or carbazolyl.

Even more preferably, R⁸ and R⁹ are each independently unsubstituted phenyl,

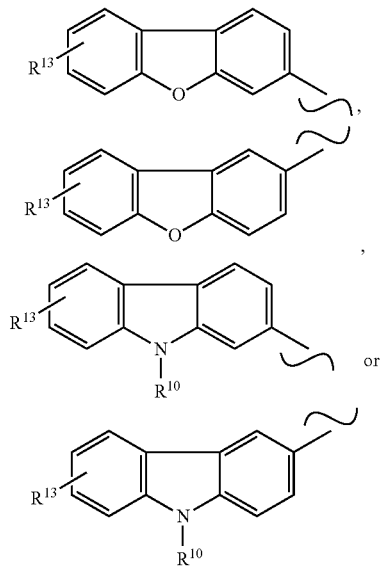

wherein R¹⁰ is $C_1$-$C_{20}$-alkyl, $C_6$-$C_{30}$-aryl, heteroaryl having 5 to 30 ring atoms, —O—Si($C_1$-$C_{20}$-alkyl)₃, —O—Si($C_6$-$C_{30}$-aryl)₃, $C_1$-$C_{20}$-alkoxy or $C_6$-$C_{30}$-aryloxy; preferably $C_6$-$C_{30}$-aryl, more preferably phenyl, and R¹³ is H or phenoxasilinyl of formula (I'), preferably H.

The symbol ~ means that there is a binding site at the position marked with ~. In a preferred embodiment, R⁸ and R⁹ in the compounds of formula (I) are identical.

R¹, R², R³, R⁴, R⁵, R⁶ and R⁷ in the phenoxasiline derivatives of the formula (I) are each independently hydrogen, $C_1$-$C_{20}$-alkyl, $C_3$-$C_{20}$-cycloalkyl, heterocycloalkyl having 3 to 20 ring atoms, $C_6$-$C_{30}$-aryl, heteroaryl having 5 to 30 ring atoms or a substituent with donor or acceptor action selected from the group consisting of $C_1$-$C_{20}$-alkoxy, $C_6$-$C_{30}$-aryloxy, $C_1$-$C_{20}$-alkylthio, $C_6$-$C_{30}$-arylthio, SiR¹⁰R¹¹R¹², halogen radicals, halogenated $C_1$-$C_{20}$-alkyl radicals, carbonyl (—CO(R¹⁰)), carbonylthio (—C═O (SR¹⁰)), carbonyloxy (—C═O(OR¹⁰)), oxycarbonyl (—OC═O(R¹⁰)), thiocarbonyl (—SC═O(R¹⁰)), amino (—NR¹⁰R¹¹), OH, pseudohalogen radicals, amido (—C═O (NR¹⁰)), —NR¹⁰C═O(R¹¹), phosphonate (—P(O)-(OR¹⁰)₂), phosphate (—OP(O)(OR¹⁰)₂), phosphine (—PR¹⁰R¹¹), phosphine oxide (—P(O)R¹⁰₂), sulfate (—OS (O)₂OR¹⁰), sulfoxide (—S(O)R¹⁰), sulfonate (—S(O)₂OR¹⁰), sulfonyl (—S(O)₂R¹⁰), sulfonamide (—S (O)₂NR¹⁰R¹¹), NO₂, boronic esters (—OB(OR¹⁰)₂), imino (—C═NR¹⁰R¹¹), borane radicals, stannane radicals, hydrazine radicals, hydrazone radicals, oxime radicals, nitroso groups, diazo groups, vinyl groups, sulfoximines, alanes, germanes, boroximes and borazines;

or two adjacent R¹, R², R³, R⁴, R⁵, R⁶ or R⁷ radicals, in each case together with the carbon atoms to which they are bonded, form a ring having a total of 3 to 12 atoms, where the ring may be saturated or mono- or polyunsaturated and, as well as carbon atoms, may have one or more heteroatoms selected from N, O and P, where the ring may be unsubstituted or mono- or polysubstituted and/or may be fused to further 3- to 12-membered rings.

Preferably, R¹, R², R³, R⁴, R⁵, R⁶ and R⁷ are each independently hydrogen, $C_1$-$C_{20}$-alkyl, $C_3$-$C_{20}$-cycloalkyl, heterocycloalkyl having 3 to 20 ring atoms, $C_6$-$C_{30}$-aryl, heteroaryl having 5 to 30 ring atoms, methoxy, phenyloxy, halogenated $C_1$-$C_4$-alkyl, preferably CF₃, CH₂F, CHF₂, C₂F₅, halogen, preferably F, CN, SiR¹⁰R¹¹R¹², diphenylamino or —C(O)OC₁-C₄-alkyl, preferably —C(O)OMe, P(O)Ph₂, SO₂Ph.

More preferably, R¹, R², R³, R⁴, R⁵, R⁶ and R⁷ are each independently hydrogen, $C_1$-$C_{20}$-alkyl, $C_3$-$C_{20}$-cycloalkyl, heterocycloalkyl having 3 to 20 ring atoms, $C_6$-$C_{30}$-aryl, heteroaryl having 5 to ring atoms, methoxy, phenyloxy, halogenated $C_1$-$C_4$-alkyl, preferably CF₃, CH₂F, CHF₂, C₂F₅, halogen, preferably F, CN, SiR¹⁰R¹¹R¹², P(O)Ph₂ or diphenylamino.

In one preferred embodiment, R¹, R², R³, R⁴, R⁵, R⁶ and R⁷ are each hydrogen or R¹, R², R⁵, R⁶ and R⁷ are each hydrogen and R³ and R⁴ are each independently $C_1$-$C_{20}$-alkyl, $C_3$-$C_{20}$-cycloalkyl, heterocycloalkyl having 3 to 20 ring atoms, $C_6$-$C_{30}$-aryl, heteroaryl having 5 to 30 ring atoms, methoxy, phenyloxy, halogenated $C_1$-$C_4$-alkyl, preferably CF₃, CH₂F, CHF₂, C₂F₅, halogen, preferably F, CN, SiR¹⁰R¹¹R¹², P(O)Ph₂ or diphenylamino, preferably methyl, phenyl, carbazolyl, dibenzofuryl, methoxy, phenyloxy, CF₃, CH₂F, CHF₂, C₂F₅, F, CN, SiR¹⁰R¹¹R¹², P(O)Ph₂ or diphenylamino. R³ and R⁴ may be identical or different.

In one further preferred embodiment, one of the radicals R¹, R², R³, R⁴, R⁵, R⁶ and R⁷ has the meaning mentioned before, except of hydrogen, preferably $C_1$-$C_{20}$-alkyl, $C_3$-$C_{20}$-cycloalkyl, heterocycloalkyl having 3 to 20 ring atoms, $C_6$-$C_{30}$-aryl, heteroaryl having 5 to 30 ring atoms, methoxy, phenyloxy, halogenated $C_1$-$C_4$-alkyl, preferably CF₃, CH₂F, CHF₂, C₂F₅, halogen, preferably F, CN, SiR¹⁰R¹¹R¹², P(O)Ph₂ or diphenylamino and all other radicals R¹, R², R³, R⁴, R⁵, R⁶ and R⁷ are hydrogen. Preferably, the radical which is not hydrogen is the radical R⁶. More preferably, the radical R⁶ has the same meaning as Y. Preferred meanings for Y are also preferred meanings for R⁶. Y and R⁶ may be identical or different.

In a further preferred embodiment, R⁶ as well as R³ and R⁴ have the meanings mentioned before, except of hydrogen, preferably R³ and R⁴ are $C_1$-$C_{20}$-alkyl, $C_3$-$C_{20}$-cycloalkyl, heterocycloalkyl having 3 to 20 ring atoms, $C_6$-$C_{30}$-aryl, heteroaryl having 5 to 30 ring atoms, methoxy, phenyloxy, halogenated $C_1$-$C_4$-alkyl, preferably $CF_3$, $CH_2F$, $CHF_2$, $C_2F_5$, halogen, preferably F, CN, $SiR^{10}R^{11}R^{12}$, $P(O)Ph_2$ or diphenylamino and all other radicals $R^1$, $R^2$, $R^5$ and $R^7$ are hydrogen. $R^3$ and $R^4$ may be identical or different. More preferably, the radical $R^6$ has the same meaning as Y. Preferred meanings for Y are also preferred meanings for $R^6$. Y and $R^6$ may be identical or different. Even more preferably, $R^3$ and $R^4$ are each independently methyl, phenyl, carbazolyl, dibenzofuryl, methoxy, phenyloxy, $CF_3$, $CH_2F$, $CHF_2$, $C_2F_5$, F, CN, $SiR^{10}R^{11}R^{12}$, $P(O)Ph_2$ or diphenylamino.

In a preferred embodiment of the present invention, the compound of formula (I) is selected from the compounds of formulae (Ia), (Ib), (Ic) and (Id)

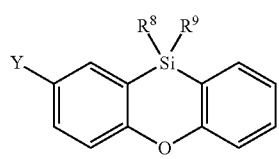
(Ia)

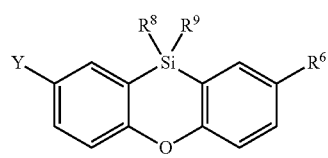
(Ib)

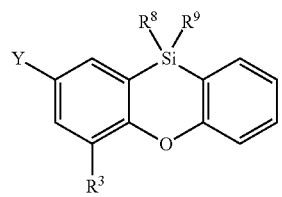
(Ic)

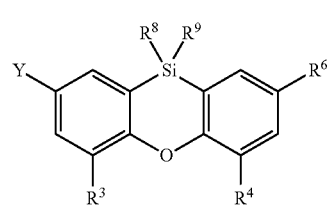
(Id)

wherein the radicals $R^3$, $R^4$, $R^6$, $R^8$, $R^9$ and Y having the meanings mentioned before, preferably, the radical $R^6$ has the same meaning as Y. Preferred meanings for Y are also preferred meanings for $R^6$, whereby Y and $R^6$ in formulae (Ib) and (Id) may be identical or different.

In a more preferred embodiment of the present invention, the compound of formula (I) is selected from the compounds of formulae (Ib) and (Id).

Examples for most preferred compounds of the formula (I) are

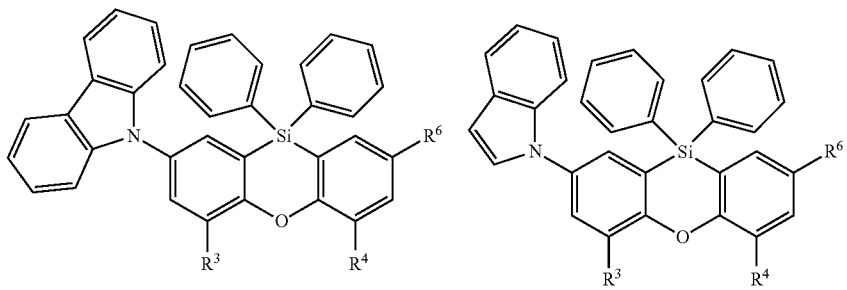

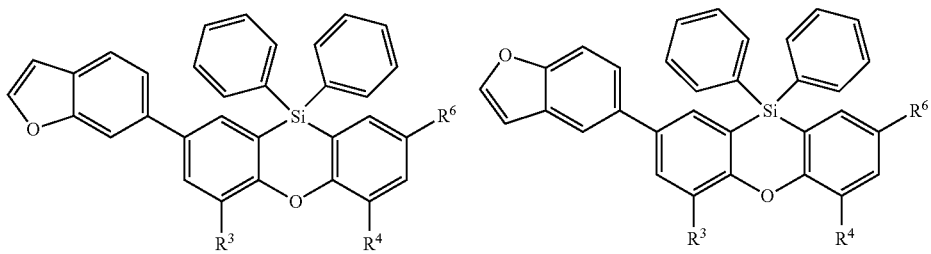

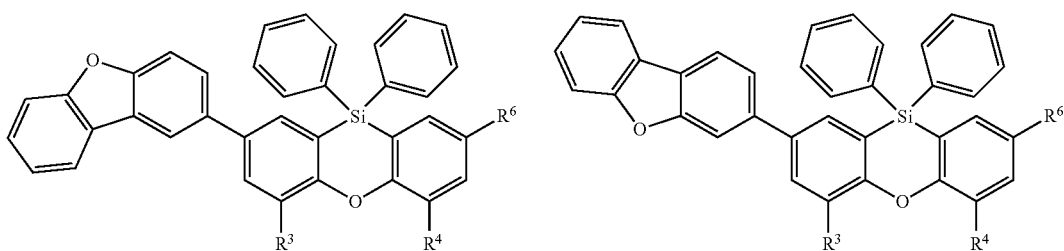

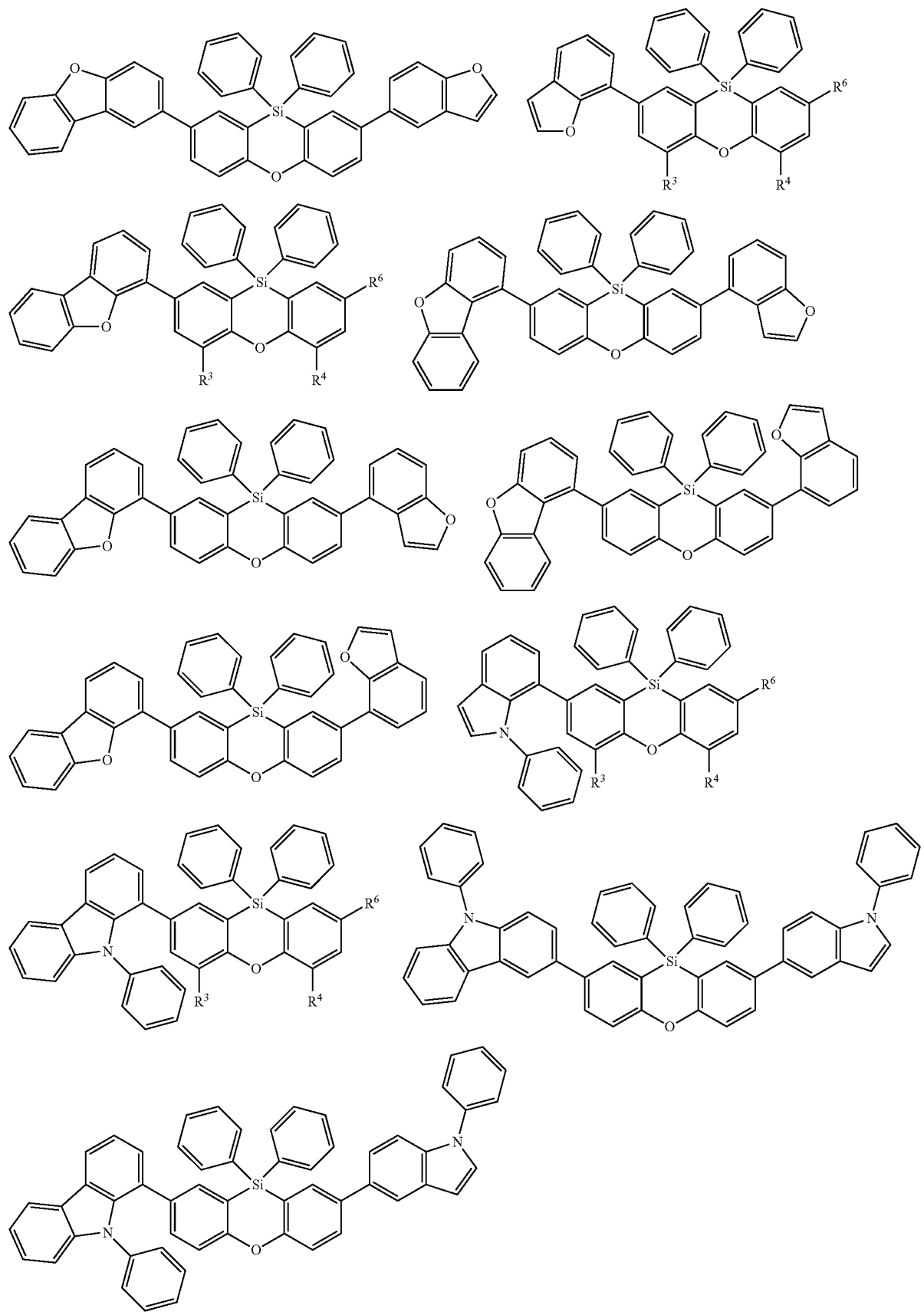

-continued
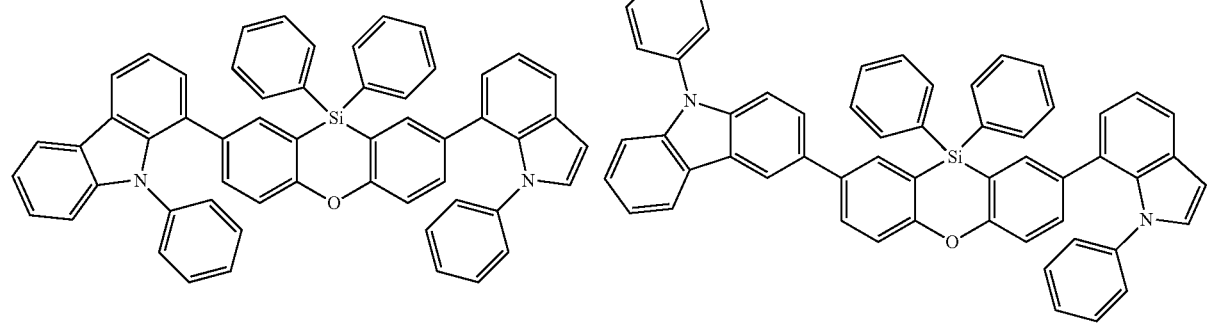
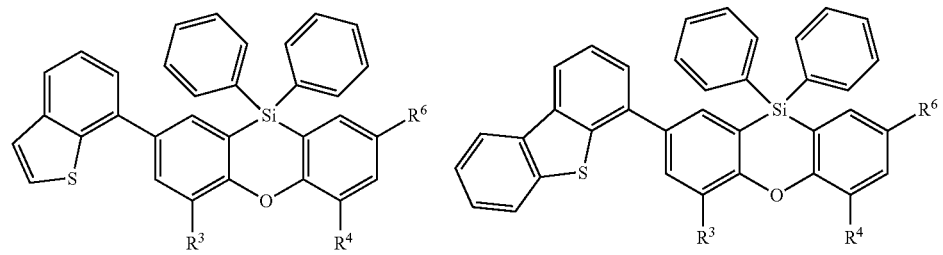
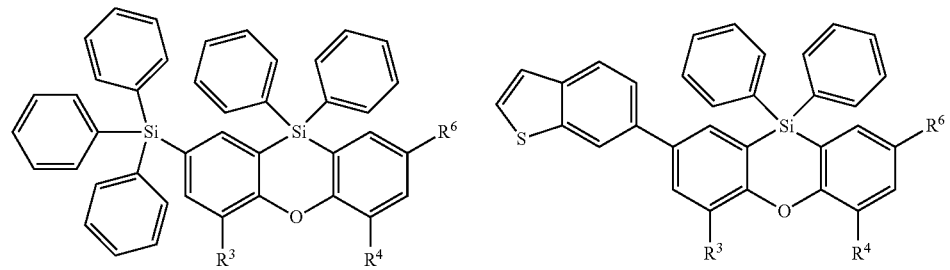
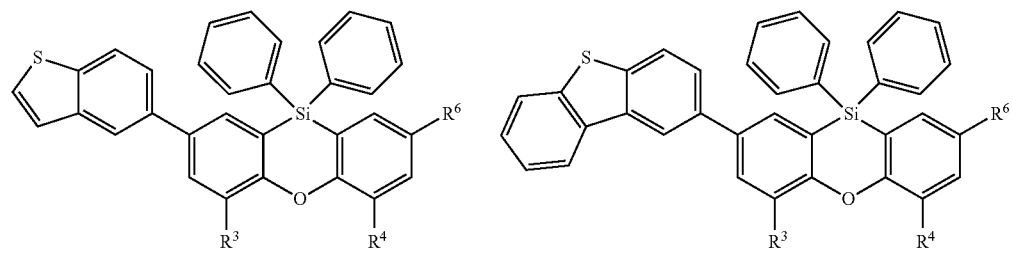
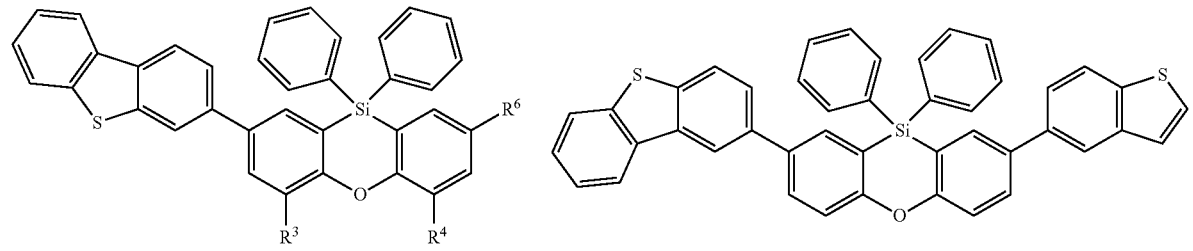
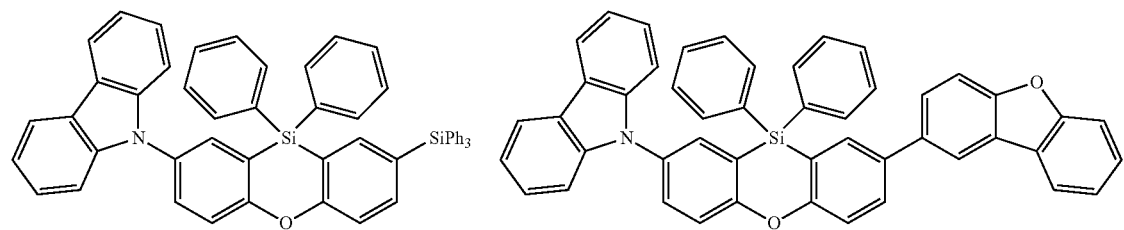

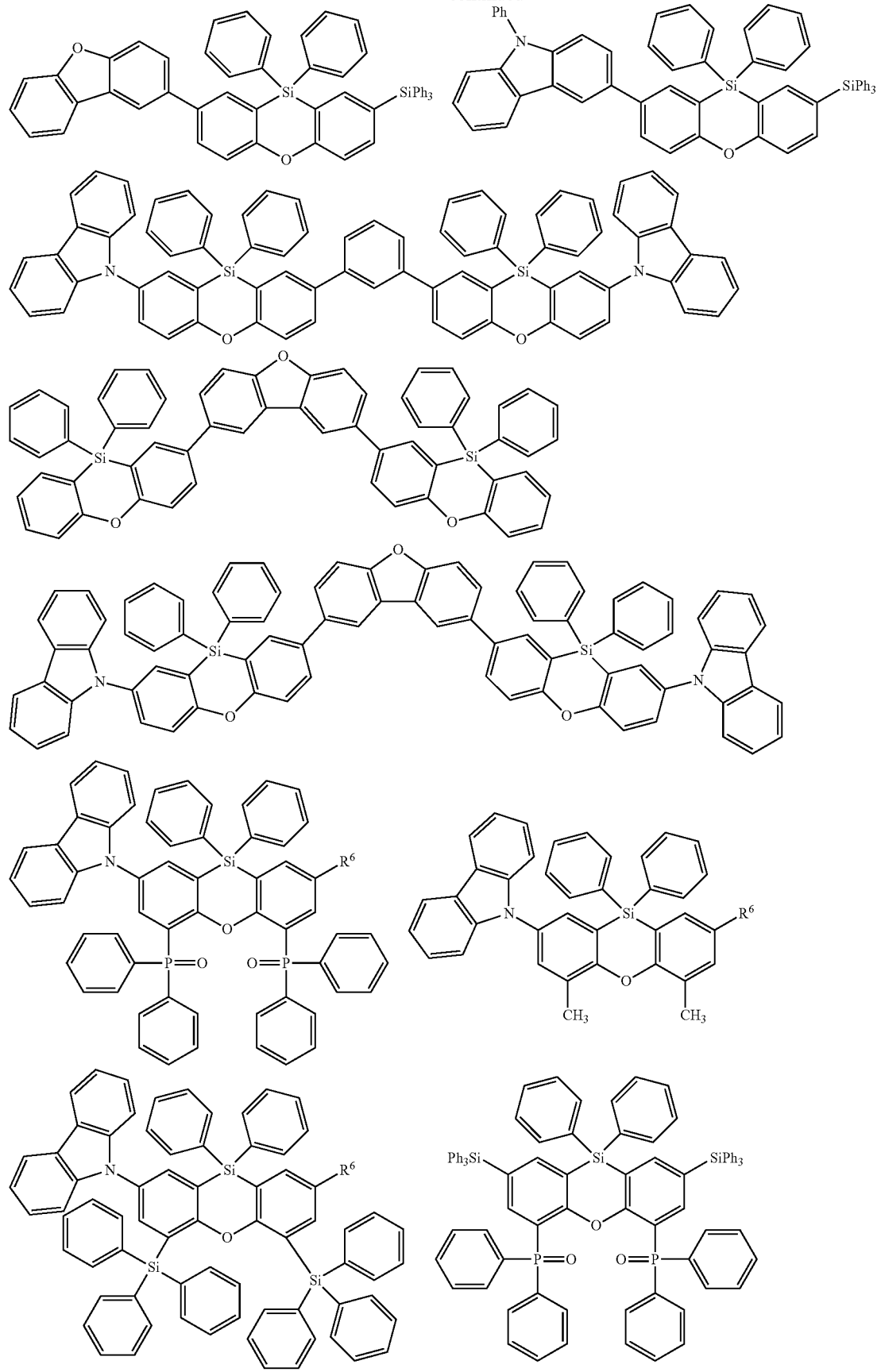

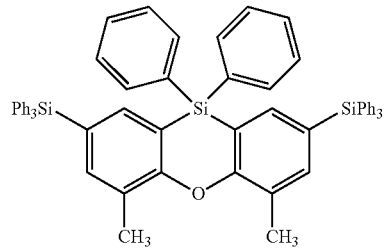
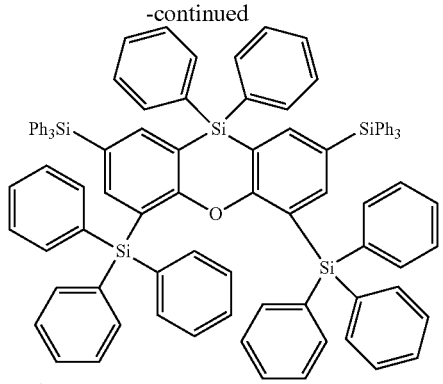
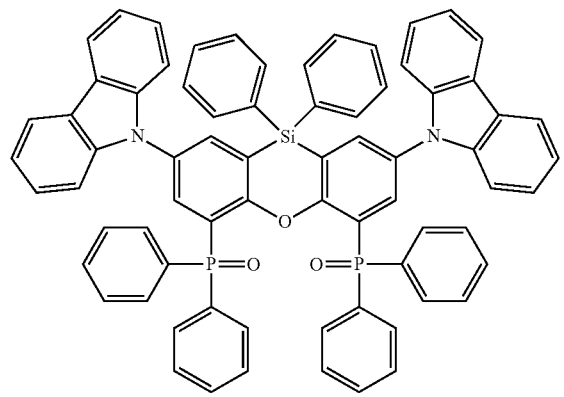
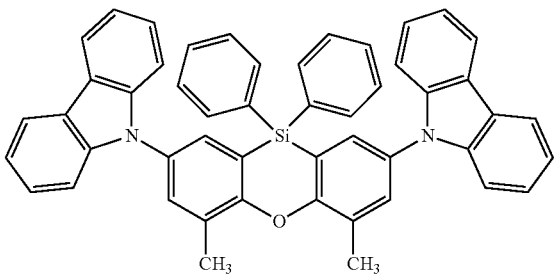
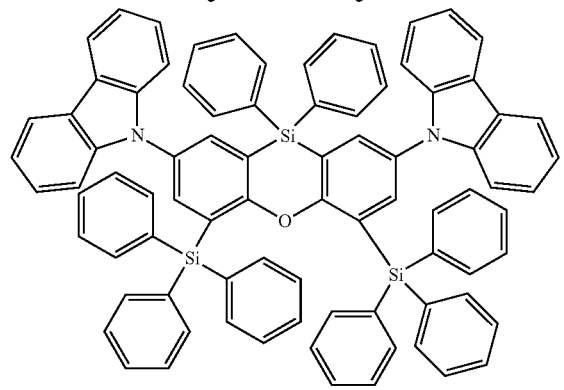
wherein
$R^6$ is selected from the group consisting of hydrogen,
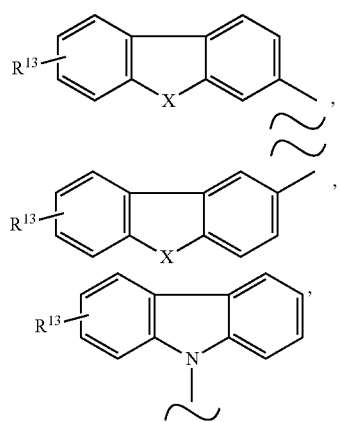
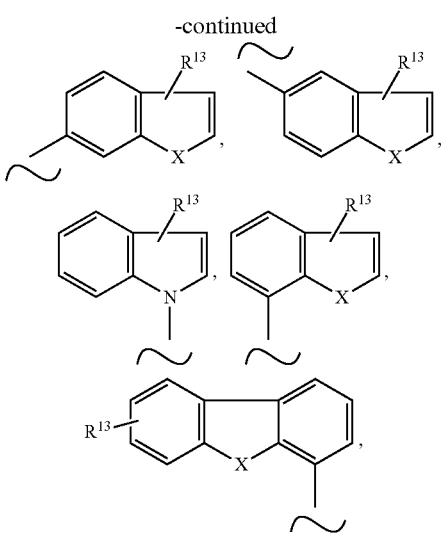

-continued

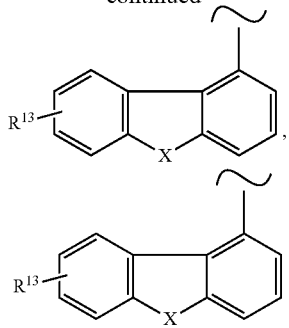

and SiPh₃,
wherein
X is NPh, O or S,
R³, R⁴ are independently of each other methyl, phenyl, carbazolyl, dibenzofuryl, methoxy, phenyloxy, $CF_3$, $CH_2F$, $CHF_2$, $C_2F_5$, F, CN, $SiR^{10}R^{11}R^{12}$, $P(O)Ph_2$ or diphenylamino, and
$R^{13}$ is H or phenoxasilinyl of formula (I'), preferably H.

The symbol ~ means that there is a binding site at the position marked with ~.

Preferably, $R^6$ is selected from the group consisting of

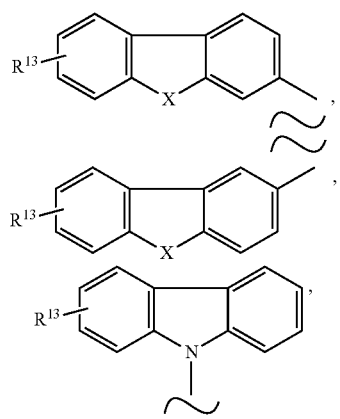

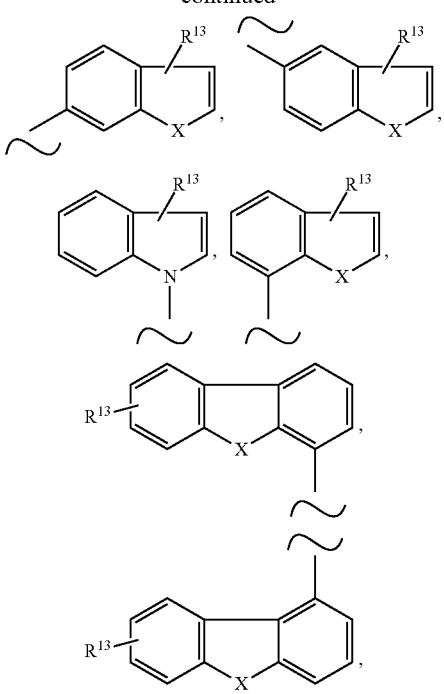

and SiPh₃,
wherein
X is NPh or O, and
$R^{13}$ is H or phenoxasilinyl of formula (I'), preferably H.

The symbol ~ means that there is a binding site at the position marked with ~.

Most preferred compounds of the formula (I) are

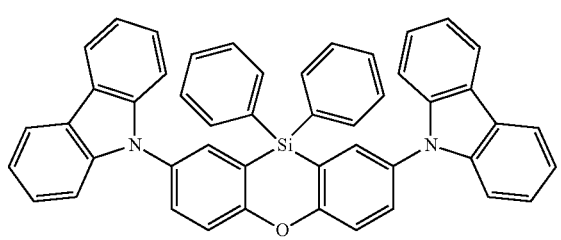

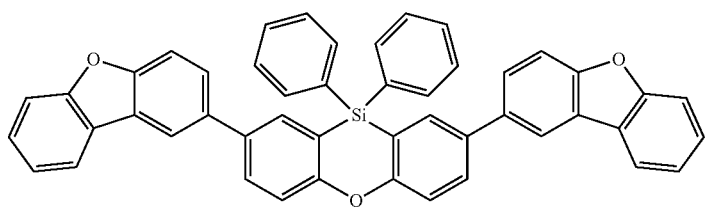

-continued
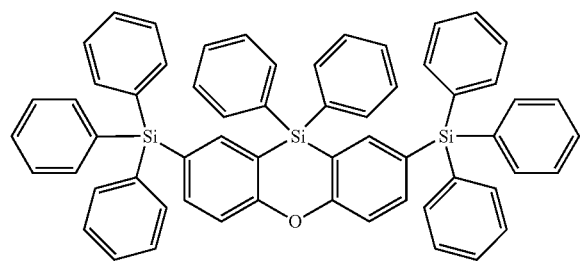
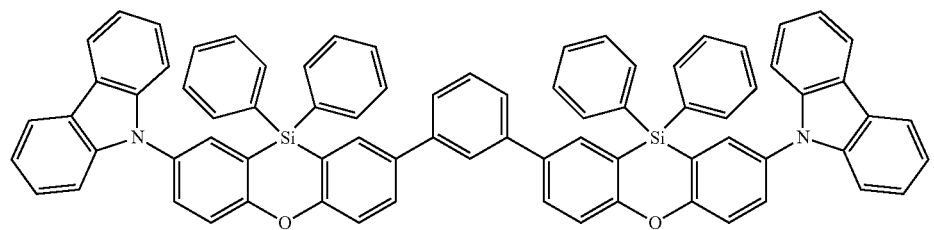
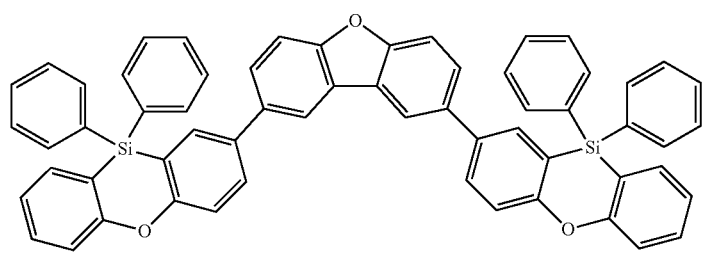
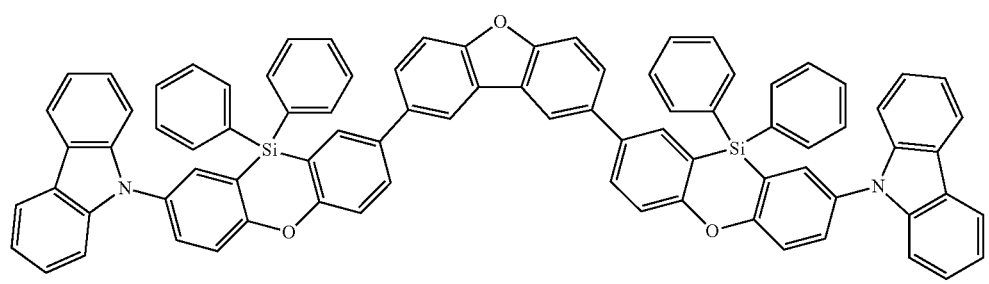
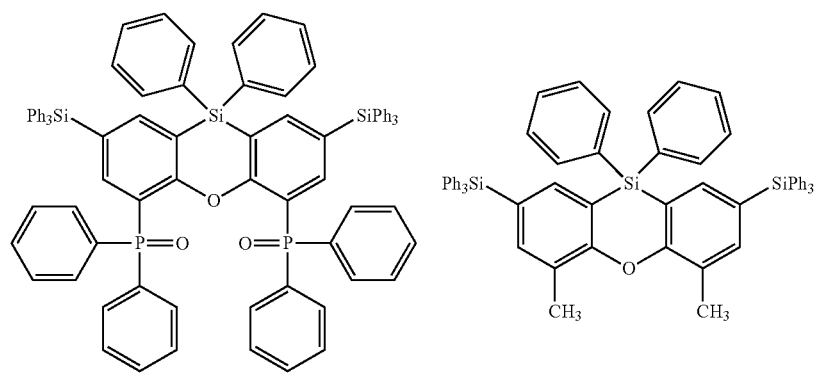

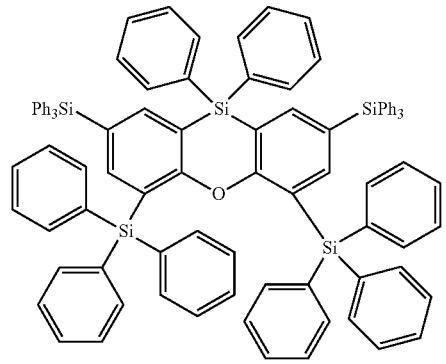
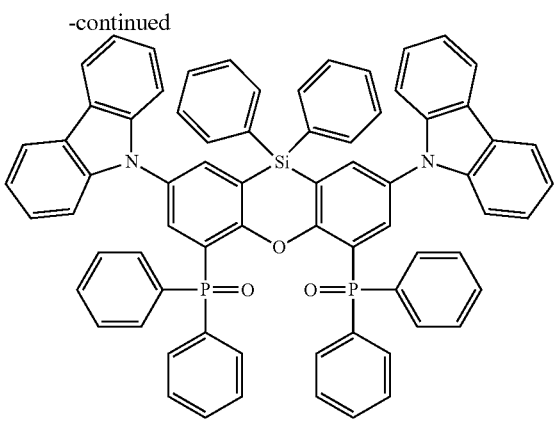
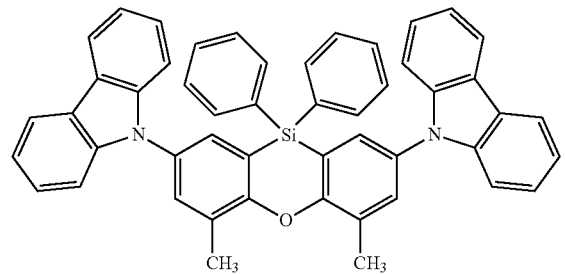
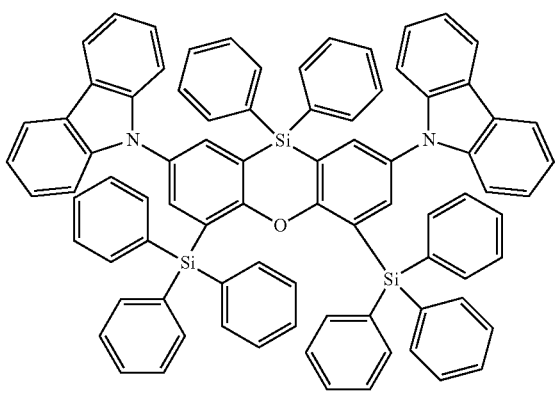
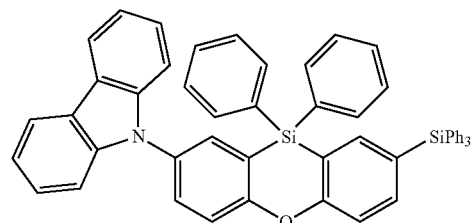
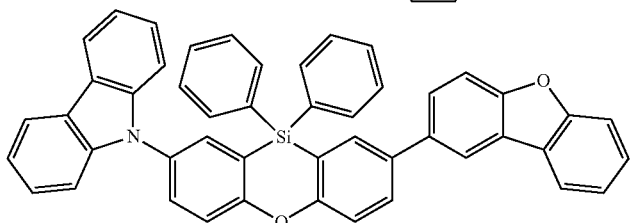
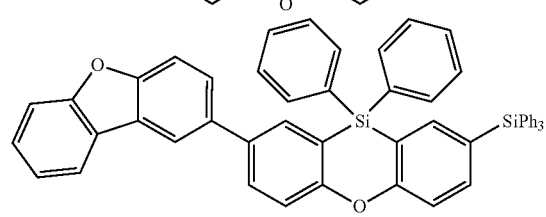
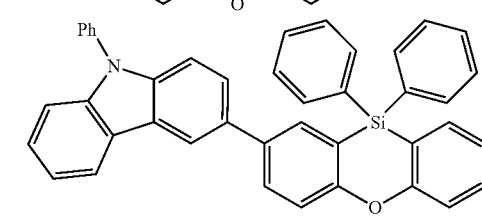

The compounds of the formula (I) can be prepared by the following process:

1) Preparation of a Functionalized Phenoxasiline Building Block (A)

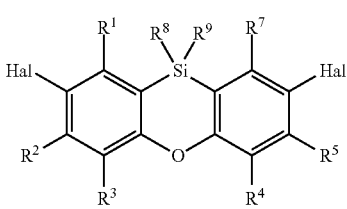

for the case that $R^6$ is not H.

In the case that $R^6$ is H, the Hal substituent at the position of $R^6$ has to be replaced by H.

wherein the radicals $R^1$, $R^2$, $R^3$, $R^4$, $R^5$, $R^7$, $R^8$ and $R^9$ have the meanings mentioned above, and Hal is Br or Cl.

Ii) Step i) Preparation of a Halogenated Diphenyl Ether

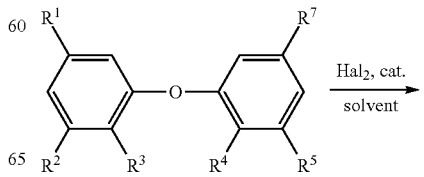

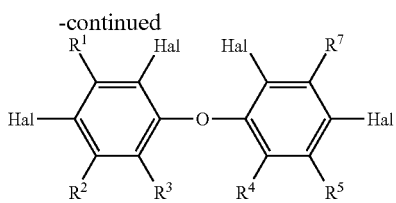

wherein the radicals $R^1$, $R^2$, $R^3$, $R^4$, $R^5$ and $R^7$ have the meanings mentioned above, and $Hal_2$ is $Br_2$ or $Cl_2$ cat. is a catalyst, preferably Fe, and solvent is a solvent, preferably an aprotic solvent, more preferably $CCl_4$.

In a preferred embodiment, the diphenyl ether, the catalyst and the solvent are heated to usually 50° C. to 100° C., preferably 60° C. to 90° C., for usually 1 to 100 hours, preferably 6 to 50 hours. Then $Hal_2$ is added in an aprotic solvent, preferably the same solvent as mentioned before, and the temperature is usually kept at 50° C. to 100° C., preferably 60° C. to 90° C. for usually 10 minutes to 6 hours, preferably 30 minutes to 1.5 hours. The reaction mixture is then worked up as known by a person skilled in the art. The obtained product is preferably further purified by recrystallization.

The catalyst is usually employed in catalytic amounts relative to the diphenyl ether (molar ratio). The molar ratio of catalyst to diphenyl ether is preferably 0.01 to 0.1:1, more preferably 0.03 to 0.08:1.

The $Hal_2$ is usually employed in an excess relative to the diphenyl ether (molar ratio). The molar ratio of $Hal_2$ to diphenyl ether is preferably 1.5 to 10:1, more preferably 2.5 to 8:1.

Iii) Step ii) Preparation of a Functionalized Phenoxasiline Building Block (A)

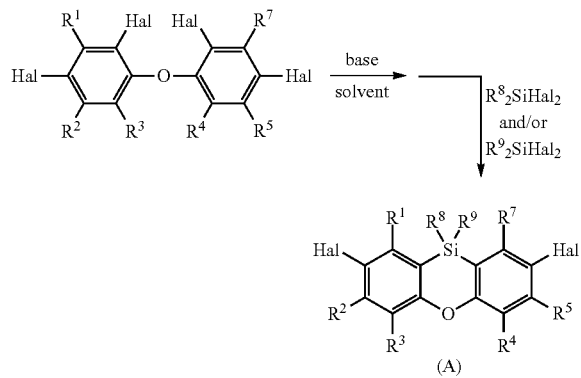

wherein the radicals $R^1$, $R^2$, $R^3$, $R^4$, $R^5$, $R^7$, $R^8$ and $R^9$ have the meanings mentioned above, and Hal is Br or Cl base is a base, preferably n-BuLi, and solvent is a protic solvent, preferably $Et_2O$.

In a preferred embodiment, the halogenated diphenyl ether of step i) is mixed in the solvent mentioned above with the base, preferably n-BuLi, at usually −50° C. to −5° C., preferably at −20° C. to −7° C. The base is preferably added dropwise. Thereafter, the mixture is stirred usually at room temperature for usually 1 to 10 hours, preferably 1.5 to 5 hours. The mixture is then cooled to usually −100° C. to −30° C., preferably −80° C. to −50° C. and $R^8{}_2SiHal_2$ and/or $R^9{}_2SiHal_2$, in an example: dichlorodiphenylsilane, is added, preferably dropwise. The resultant mixture is stirred usually at room temperature for usually 1 to 30 hours, preferably 5 to 25 hours and the precipitate obtained was usually filtered before further work-up. The reaction mixture is then worked up as known by a person skilled in the art. The obtained product is preferably further purified by chromatography.

The $R^8{}_2SiHal_2$ and/or $R^9{}_2SiHal_2$ is usually employed in equimolar amounts relative to the halogenated diphenyl ether (molar ratio). The molar ratio of $R^8{}_2SiHal_2$ and/or $R^9{}_2SiHal_2$ to halogenated diphenyl ether is preferably 1.5:1, more preferably 1.3 to 1:1. If $R^8{}_2SiHal_2$ and $R^9{}_2SiHal_2$ are employed, $R^8{}_2SiHal_2$ and $R^9{}_2SiHal_2$ are employed in equimolar amounts and the sum of $R^8{}_2SiHal_2$ and $R^9{}_2SiHal_2$ is the molar amount mentioned before in relation to the halogenated diphenyl ether.

Iiii) Step iii) Introduction of $R^3$ and $R^4$ into Building Block (A)

In the case that $R^3$ and/or $R^4$ in the compound of formula (I) are not hydrogen and are not present in building block (A) at the end of step ii), the functionalization of the ortho position in building block (A) (i.e. the position of $R^3$ and $R^4$) can be carried out as described for example in Advanced Synthesis & Catalysis 353(9), 1479-1484, 2011 and Angewandte Chemie, International Edition, 45(35), 5803-5807; 2006.

In a typical procedure a deprotonation and activation of the ortho position in building block (A) is carried out by deprotonation with for example s-butyl lithium in for example TMEDA (tetramethylethylene diamine) and activation with chloride (e.g. by addition of $PPh_2Cl$ or $SiPh_3Cl$) or iodide (e.g. by addition of alkyl iodide, e.g. methyl iodide).

The activated ortho position can then be substituted as known by a person skilled in the art, for example in the case of a functionalization with $P(O)Ph_2$, by functionalization with $PPh_2Cl$ and a subsequent oxidation with for example mCPBA (meta-chloroperbenzoic acid).

It is also possible to carry step Iiii) out after the coupling in step II) is carried out.

II) Preparation of the Phenoxasilines According to the Present Invention

The functionalized phenoxasiline building block (A) is the preferred starting material for the preparation of the compounds of formula (I) of the present invention. The groups Y and (optionally) $R^6$ are introduced into the building block (A) by coupling methods known by a person skilled in the art. In the examples the introduction of three different ligand types is described:

i) Groups Y and $R^6$ are bonded via a heteroatom in a heterocyclic ring system (e.g. carbazolyl bonded via N; compound (1)). Such groups are preferably introduced into the building block (A) by Ullmann coupling or Buchwald coupling. An example for a suitable coupling reaction is given in synthesis example I.2.

ii) Groups Y and $R^6$ are bonded via a heteroatom which is not in a heterocyclic ring system (e.g. —$SiPh_3$ bonded via Si; compound (2)). Such coupling reactions are known to a person skilled in the art. An example for a suitable coupling reaction is given in synthesis example 1.3.

iii) Groups Y and $R^6$ are bonded via an aromatic carbon atom (e.g. dibenzofuranyl bonded via an aromatic C; compound (3)). Such groups are preferably introduced into the building block (A) by Suzuki coupling or Yamamoto coupling. An example for a suitable coupling reaction is given in synthesis example I.4.

The phenoxasiline derivatives of the general formula (I) are suitable for use in organic electronics applications, especially in OLEDs. Further organic electronics applications have been mentioned before.

The phenoxasiline derivatives of the general formula (I) are useful in any layer of organic electronic applications, especially OLEDs. Preferably, the phenoxasiline derivatives of the general formula (I) are employed as host (matrix) material, preferably in the light-emitting layer, in OLEDs, or as electron/hole/exciton transport material, or as electron/hole/exciton blocker material or electron/hole/exciton injection material in the respective layer of organic electronics applications, especially OLEDs or as organic semiconductor layer.

Suitable structures of the organic electronics applications are known to those skilled in the art and are specified below.

The organic transistor generally includes a semiconductor layer formed from an organic layer with hole transport capacity and/or electron transport capacity; a gate electrode formed from a conductive layer; and an insulation layer introduced between the semiconductor layer and the conductive layer. A source electrode and a drain electrode are mounted on this arrangement in order thus to produce the transistor element. In addition, further layers known to those skilled in the art may be present in the organic transistor. The compounds of the formula (I) may be present in any desired layer of the organic transistor.

The organic solar cell (photoelectric conversion element) generally comprises an organic layer present between two plate-type electrodes arranged in parallel. The organic layer may be configured on a comb-type electrode. There is no particular restriction regarding the site of the organic layer and there is no particular restriction regarding the material of the electrodes. When, however, plate-type electrodes arranged in parallel are used, at least one electrode is preferably formed from a transparent electrode, for example an ITO electrode or a fluorine-doped tin oxide electrode. The organic layer is formed from two sublayers, i.e. a layer with p-type semiconductor character or hole transport capacity, and a layer formed with n-type semiconductor character or electron transport capacity. In addition, it is possible for further layers known to those skilled in the art to be present in the organic solar cell. The compounds of the formula (I) may be present in any desired layer of the organic solar cell.

Preferably, the present invention relates to an organic light-emitting diode comprising at least one compound of the formula (I). The compounds of the formula (I) can be used in the organic light-emitting diode as host (matrix) material and/or hole/exciton blocker material and/or electron/exciton blocker material and/or hole injection material and/or electron injection material and/or hole conductor material and/or electron conductor material, preferably as host (matrix) material, preferably in the light-emitting layer, and/or as electron/hole/exciton transport material and/or as electron/hole/exciton blocker material and/or electron/hole/exciton injection material.

The present invention therefore relates to the inventive organic electronics applications, wherein at least one compound of formula (I) is employed as host (matrix) material, preferably in the light-emitting layer, and/or as electron/hole/exciton transport material and/or as electron/hole/exciton blocker material and/or electron/hole/exciton injection material.

The present invention further relates to host (matrix) material and/or electron/hole/exciton transport material and/or electron/hole/exciton blocker material and/or electron/hole/exciton injection material in organic electronics applications comprising at least one compound of the formula (I) according to the present invention.

The compounds of the general formula (I) may be employed alone or in a mixture, for example together with another host (matrix) material, electron/hole/exciton transport material, electron/hole/exciton blocker material or electron/hole/exciton injection material. Further host (matrix) material, electron/hole/exciton transport material, electron/hole/exciton blocker material and electron/hole/exciton injection material used may generally be materials known to those skilled in the art, especially the host (matrix) material, electron/hole/exciton transport material, electron/hole/exciton blocker material and electron/hole/exciton injection material mentioned below.

It is likewise possible that the compounds of the formula (I) are present in more than one layer of the organic electronics applications, especially OLEDs, for example in both in the light-emitting layer (as host (matrix) material) and in the blocking layer for holes.

In a further embodiment, the present invention concerns the use of a compound of formula (I) according to the present invention in organic electronics applications. Suitable organic electronics applications are mentioned before. Preferred organic electronics applications are OLEDs.

The present invention further provides an organic light-emitting diode comprising an anode An and a cathode Ka and a light-emitting layer E arranged between the anode An and the cathode Ka, and optionally at least one further layer selected from the group consisting of at least one blocking layer for holes/excitons, at least one blocking layer for electrons/excitons, at least one hole injection layer, at least one hole conductor (transport) layer, at least one electron injection layer and at least one electron conductor (transport) layer, wherein the at least one compound of the formula (I) is present in the light-emitting layer E and/or in at least one of the further layers. The at least one compound of the formula (I) is preferably present in the light-emitting layer as a host and/or in the blocking layer for holes/excitons. The at least one compound of the formula (I) may further or additionally be present in the electron/exciton transport layer, hole/exciton transport layer, electron/exciton blocking layer, hole/exciton injection layer and/or electron/exciton injection layer The present application further relates to a light-emitting layer comprising at least one compound of the formula (I), preferably as host.

The present invention further relates to an OLED comprising an inventive light-emitting layer.

The present invention further relates to a electron/exciton transport layer or hole/exciton transport layer comprising at least one compound of the formula (I).

The present invention further relates to a blocking layer for holes/excitons or a blocking layer for electrons/excitons comprising at least one compound of the formula (I).

The present invention further relates to an injection layer for holes/excitons or an injection layer for electrons/excitons comprising at least one compound of the formula (I).

Structure of the inventive OLED The inventive organic light-emitting diode (OLED) thus generally has the following structure:

An anode (An) and a cathode (Ka) and a light-emitting layer E arranged between the anode (An) and the cathode (Ka).

The inventive OLED may, for example—in a preferred embodiment—be formed from the following layers:
1. anode
2. hole conductor (transport) layer 3. light-emitting layer
4. blocking layer for holes/excitons
5. electron conductor (transport) layer
6. cathode Layer sequences different from the aforementioned construction are also possible, and are known to those skilled in the art. For example, it is possible that the OLED does not have all of the layers mentioned; for example, an OLED with the layers (1) (anode), (3) (light-emitting layer) and (6) (cathode) are likewise suitable, in which case the functions of the layers (2) (hole conductor layer) and (4) (blocking layer for holes/excitons) and (5) (electron conductor layer) are assumed by the adjoining layers. OLEDs which have layers (1), (2), (3) and (6), or layers (1), (3), (4), (5) and (6), are likewise suitable. In addition, the OLEDs may have a blocking layer for electrons/excitons between the anode (1) and the hole conductor layer (2).

It is additionally possible that a plurality of the aforementioned functions (electron/exciton blocker, hole/exciton blocker, hole injection, hole conduction, electron injection, electron conduction) are combined in one layer and are assumed, for example, by a single material present in this layer. For example, a material used in the hole conductor layer, in one embodiment, may simultaneously block excitons and/or electrons.

Furthermore, the individual layers of the OLED among those specified above may in turn be formed from two or more layers. For example, the hole conductor layer may be formed from a layer into which holes are injected from the electrode, and a layer which transports the holes away from the hole-injecting layer into the light-emitting layer. The electron conduction layer may likewise consist of a plurality of layers, for example a layer in which electrons are injected by the electrode, and a layer which receives electrons from the electron injection layer and transports them into the light-emitting layer. These layers mentioned are each selected according to factors such as energy level, thermal resistance and charge carrier mobility, and also energy difference of the layers specified with the organic layers or the metal electrodes. The person skilled in the art is capable of selecting the structure of the OLEDs such that it is matched optimally to the organic compounds used as emitter substances in accordance with the invention.

In order to obtain particularly efficient OLEDs, for example, the HOMO (highest occupied molecular orbital) of the hole conductor layer should be matched to the work function of the anode, and the LUMO (lowest unoccupied molecular orbital) of the electron conductor layer should be matched to the work function of the cathode, provided that the aforementioned layers are present in the inventive OLEDs.

The anode (1) is an electrode which provides positive charge carriers. It may be formed, for example, from materials which comprise a metal, a mixture of various metals, a metal alloy, a metal oxide or a mixture of various metal oxides. Alternatively, the anode may be a conductive polymer. Suitable metals comprise metals and alloys of the metals of the main groups, transition metals and of the lanthanoids, especially the metals of groups Ib, IVa, Va and VIa of the periodic table of the elements, and the transition metals of group VIIIa. When the anode is to be transparent, generally mixed metal oxides of groups IIb, IIIb and IVb of the Periodic Table of the Elements (old IUPAC version) are used, for example indium tin oxide (ITO). It is likewise possible that the anode (1) comprises an organic material, for example polyaniline, as described, for example, in Nature, vol. 357, pages 477 to 479 (Jun. 11, 1992). At least either the anode or the cathode should be at least partly transparent in order to be able to emit the light formed. The material used for the anode (1) is preferably ITO.

Suitable hole conductor materials for layer (2) of the inventive OLEDs are disclosed, for example, in Kirk-Othmer Encyclopedia of Chemical Technology, 4th edition, vol. 18, pages 837 to 860, 1996. Both hole-transporting molecules and polymers can be used as hole transport material. Hole-transporting molecules typically used are selected from the group consisting of tris[N(1-naphthyl)-N-(phenylamino)]triphenylamine (1-NaphDATA), 4,4'-bis[N-(1-naphthyl)-N-phenylamino]biphenyl (α-NPD), N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)N,N'-bis(4-ethylphenyl)-[, 1'-(3,3'-dimethyl)biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl)](4-methylphenyl)methane (MPMP), 1-phenyl-3-[p(diethylamino)styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), 4,4',4"-tris(N,N-diphenylamino)triphenylamine (TDTA), 4,4',4"-tris(N-carbazolyl)triphenylamine (TCTA), N,N'-bis(naphthalen-2-yl)-N,N'-bis(phenyl)benzidine (β-NPB), N,N'-bis(3-methylphenyl)-N,N'-bis(phenyl)-9,9-spirobifluorene (spiro-TPD), N,N'-bis(naphthalen-1-yl)-N,N'-bis(phenyl)-9,9-spirobifluorene (spiro-NPB), N,N'-bis(3-methylphenyl)-N,N'-bis(phenyl)-9,9-dimethylfluorene (DMFL-TPD), di[4-(N,N-ditolylamino)phenyl]cyclohexane, N,N'-bis(naphthalen-1-yl)-N,N'-bis(phenyl)-9,9-dimethylfluorene, N,N'-bis(naphthalen-1-yl)-N,N'-bis(phenyl)-2,2-dimethylbenzidine, N,N'-bis(naphthalen-1-yl)-N,N'-bis(phenyl)benzidine, N,N'-bis(3-methylphenyl)-N,N'-bis(phenyl)benzidine, 2,3,5,6-tetrafluoro-7,7,8,8-tetracyanoquinodimethane (F4-TCNQ), 4,4',4"-tris(N-3-methylphenyl-N-phenylamino)triphenylamine, 4,4',4"-tris(N-(2-naphthyl)-N-phenyl-amino)triphenylamine, pyrazino[2,3-f][1,10]phenanthroline-2,3-dicarbonitrile (PPDN), N,N,N',N'-tetrakis(4-methoxyphenyl)benzidine (MeO-TPD), 2,7-bis[N,N-bis(4-methoxyphenyl)amino]-9,9-spirobifluorene (MeO-spiro-TPD), 2,2'-bis[N,N-bis(4-methoxyphenyl)amino]-9,9-spirobifluorene (2,2'-MeO-spiro-TPD), N,N'-diphenyl-N,N'-di[4-(N,N-ditolylamino)phenyl]benzidine (NTNPB), N,N'-diphenyl-N,N'-di[4-(N,N-diphenylamino)phenyl]benzidine (NPNPB), N,N'-di(naphthalen-2-yl)-N,N'-diphenylbenzene-1,4-diamine (β-NPP), N,N'-bis(3-methylphenyl)-N,N'-bis(phenyl)-9,9-diphenylfluorene (DPFL-TPD), N,N'-bis(naphthalen-1-yl)-N,N'-bis(phenyl)-9,9-diphenylfluorene (DPFL-NPB), 2,2',7,7'-tetrakis(N,N-diphenylamino)-9,9'-spirobifluorene (spiro-TAD), 9,9-bis[4-(N,N-bis(biphenyl-4-yl)amino)phenyl]-9H-fluorene (BPAPF), 9,9-bis[4-(N,N-bis(naphthalen-2-yl)amino)phenyl]-9H-fluorene (NPAPF), 9,9-bis[4-(N,N-bis(naphthalen-2-yl)-N,N'-bisphenylamino)phenyl]-9H-fluorene (NPBAPF), 2,2',7,7'-tetrakis[N-naphthalenyl(phenyl)amino]-9,9'-spirobifluorene (spiro-2NPB), N,N'-bis(phenanthren-9-yl)-N,N'-bis(phenyl)benzidine (PAPB), 2,7-bis[N,N-bis(9,9-spirobifluoren-2-yl)amino]-9,9-spirobifluorene (spiro-5), 2,2'-bis[N,N-bis(biphenyl-4-yl)amino]-9,9-spirobifluorene (2,2'-spiro-DBP), 2,2'-bis(N,N-diphenylamino)-9,9-spirobifluorene (spiro-BPA), 2,2',7,7'-tetra(N,N-ditolyl)aminospirobifluorene (spiro-TTB), N,N,N',N'-tetranaphthalen-2-ylbenzidine (TNB), porphyrin compounds and phthalocyanines such as copper phthalocyanines and titanium oxide phthalocyanines. Hole-transporting polymers typically used are selected from the group consisting of polyvinylcarbazoles, (phenylmethyl)polysilanes and polyanilines. It is likewise possible to obtain hole-transporting polymers by doping hole-transporting molecules into polymers such as polystyrene and polycarbonate. Suitable hole-transporting molecules are the molecules already mentioned above.

In addition—in one embodiment—it is possible to use carbene complexes as hole conductor materials, the band gap of the at least one hole conductor material generally being greater than the band gap of the emitter material used. In the context of the present application, "band gap" is understood to mean the triplet energy. Suitable carbene complexes are, for example, carbene complexes as described in WO 2005/019373 A2, WO 2006/056418 A2, WO 2005/113704, WO 2007/115970, WO 2007/115981 and WO 2008/000727. One example of a suitable carbene complex is Ir(dpbic)$_3$ with the formula:

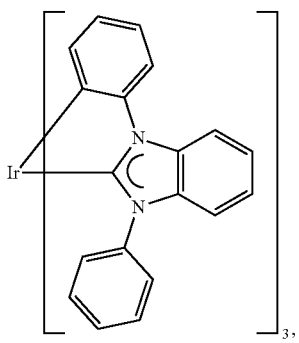

which is disclosed, for example, in WO2005/019373. In principle, it is also possible that the hole conductor layer comprises at least one compound of the formula (I) as a hole conductor material.

It is likewise possible to use mixtures in the hole-transporting (hole-conducting) layer, in particular mixtures which lead to electrical p-doping of the hole-transporting layer. p-doping is achieved by the addition of oxidizing materials. These mixtures may, for example, be mixtures of the abovementioned hole transport materials with MoO$_2$, MoO$_3$, WO$_x$, ReO$_3$, V$_2$O$_5$, 7,7,8,8-tetracyanoquinodimethane (TCNQ), 2,3,5,6-tetrafluoro-7,7,8,8-tetracyanoquinodimethane (F$_4$-TCNQ), 2,5-bis(2-hydroxyethoxy)-7,7,8,8-tetracyanoquinodimethane, bis(tetra-n-butylammonium) tetracyanodipheno-quinodimethane, 2,5-dimethyl-7,7,8,8-tetracyanoquinodimethane, tetracyanoethylene, 11,11,12,12-tetracyanonaphtho-2,6-quinodimethane, 2-fluoro-7,7,8,8-tetracyanoquino-dimethane, 2,5-difluoro-7,7,8,8-tetracyanoquinodimethane, dicyanomethylene-(1,3,4,5,7,8-hexafluoro-6H-naphthalen-2-ylidene)malononitrile (F$_6$-TNAP), Mo(tfd)$_3$ (from Kahn et al., J. Am. Chem. Soc. 2009, 131 (35), 12530-12531), and with quinone compounds as mentioned in EP 09153776.1.

The light-emitting layer (3) comprises at least one emitter material. This may in principle be a fluorescence or phosphorescence emitter, suitable emitter materials being known to those skilled in the art. The at least one emitter material is preferably a phosphorescence emitter. The phosphorescence emitter compounds used with preference are based on metal complexes, and especially the complexes of the metals Ru, Rh, Ir, Pd and Pt, in particular the complexes of Ir, have gained significance. The compounds of the formula (I) can be used as host (matrix) in the light-emitting layer. It is possible to use the compounds of the formula (I) as single host in the light emitting layer or in combination with one or more further compounds. Suitable further compounds may be further compounds of the formula (I) and/or other host (matrix) materials mentioned below.

Suitable metal complexes for use in the inventive OLEDs are described, for example, in documents WO 02/60910 A1, US 2001/0015432 A1, US 2001/0019782 A1, US 2002/0055014 A1, US 2002/0024293 A1, US 2002/0048689 A1, EP 1 191 612 A2, EP 1 191 613 A2, EP 1 211 257 A2, US 2002/0094453 A1, WO 02/02714 A2, WO 00/70655 A2, WO 01/41512 A1, WO 02/15645 A1, WO 2005/019373 A2, WO 2005/113704 A2, WO 2006/115301 A1, WO 2006/067074 A1, WO 2006/056418, WO 2006121811 A1, WO 2007095118 A2, WO 2007/115970, WO 2007/115981, WO 2008/000727, WO 2012/121936 A2 and US 2011/0057559.

Suitable emitters mentioned in US 2011/0057559 are for example:

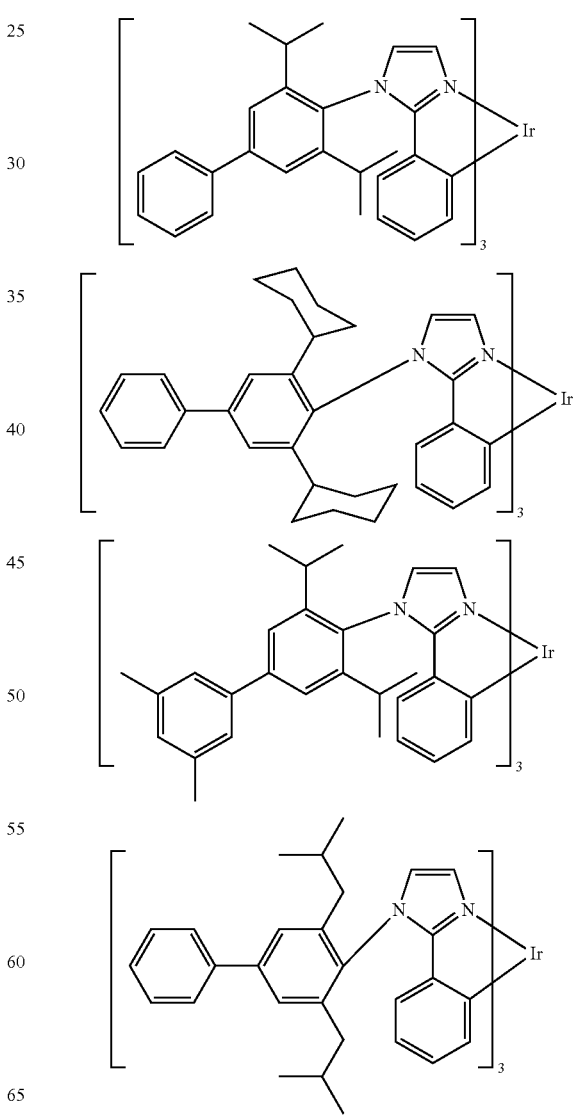

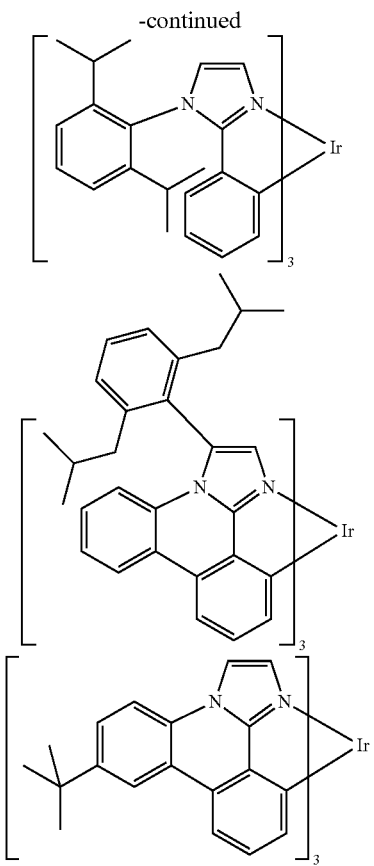

Further suitable metal complexes are the commercially available metal complexes tris(2-phenylpyridine)iridium (III), iridium(III) tris(2-(4-tolyl)pyridinato-N,C$^{2'}$), bis(2-phenylpyridine)(acetylacetonato)iridium(III), iridium(III) tris(1-phenylisoquinoline), iridium(III) bis(2,2'-benzothienyl)(pyridinato-N,C$^{3'}$)(acetylacetonate), tris(2-phenylquinoline)iridium(III), iridium(III) bis(2-(4,6-difluorophenyl)pyridinato-N,C$^2$)picolinate, iridium(III) bis(1-phenylisoquinoline)(acetylacetonate), bis(2-phenylquinoline)(acetylacetonato)iridium(III), iridium(III) bis(dibenzo[f,h]quinoxaline)-(acetylacetonate), iridium(III) bis(2-methyldibenzo[f,h]quinoxaline)(acetylacetonate) and tris(3-methyl-1-phenyl-4-trimethylacetyl-5-pyrazolino)terbium(III), bis[1-(9,9-dimethyl-9H-fluoren-2-yl)isoquinoline](acetyl-acetonato)iridium(III), bis(2-phenylbenzo-thiazolato)(acetylacetonato)iridium(III), bis(2-(9,9-dihexylfluorenyl)-1-pyridine)(acetyl-acetonato)iridium(III), bis(2-benzo[b]thiophen-2-ylpyridine)(acetylacetonato) iridium(III).

In addition, the following commercially available materials are suitable: tris(dibenzoylacetonato)mono(phenanthroline)europium(III), tris(dibenzoylmethane)mono (phenanthroline)europium(III), tris(dibenzoylmethane) mono(5-aminophenanthroline)europium(III), tris(di-2-naphthoylmethane)mono(phenanthroline)europium(III), tris (4-bromobenzoylmethane)mono(phenanthroline)europium (III), tris(di(biphenyl)methane)mono(phenanthroline) europium(III), tris(dibenzoylmethane)mono(4,7-diphenylphenanthroline)europium(III), tris (dibenzoylmethane)mono(4,7-dimethylphenanthroline) europium(III), tris(dibenzoylmethane)mono(4,7-dimethylphenanthrolinedisulfonic acid)europium(III) disodium salt, tris[di(4-(2-(2-ethoxyethoxyl)ethoxy)benzoylmethane)]mono(phenanthroline)europium(III) and tris[di [4-(2-(2-ethoxyethoxyl)ethoxy)benzoylmethane)]mono(5-aminophenanthroline)europium(III), osmium(II)bis(3-(trifluoromethyl)-5-(4-tert-butylpyridyl)-1,2,4-triazolato) diphenylmethylphosphine, osmium(II)bis(3-(trifluoromethyl)-5-(2-pyridyl)-1,2,4-triazole) dimethylphenylphosphine, osmium(II)bis(3-(trifluoromethyl)-5-(4-tert-butylpyridyl)-1,2,4-triazolato) dimethylphenylphosphine, osmium(II)bis(3-(trifluoromethyl)-5-(2-pyridyl)pyrazolato) dimethylphenylphosphine, tris[4,4'-di-tert-butyl(2,2') bipyridine]ruthenium(III), osmium(II)bis(2-(9,9-dibutylfluorenyl)-1-isoquinoline)(acetylacetonate).

Suitable triplet emitters are, for example, carbene complexes. In one embodiment of the present invention, the compounds of the formula (I) are used in the light-emitting layer as a host (matrix) material together with carbene complexes as triplet emitters. Suitable carbene complexes are, for example, carbene complexes of the general formula (II)

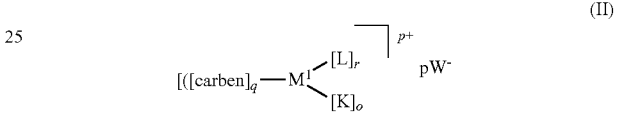

(II)

in which the symbols are each defined as follows:
M$^1$ is a metal atom selected from the group consisting of metals of group IB, IIB, IIIB, IVB, VB, VIB, VIIB, the lanthanides and IIA of the Periodic Table of the Elements (CAS version) in any oxidation state possible for the particular metal atom;
carbene is a carbene ligand which may be uncharged or monoanionic and mono-, bi- or tridentate; the carbene ligand may also be a bis- or triscarbene ligand;
L is a mono- or dianionic ligand, preferably monoanionic ligand, which may be mono- or bidentate;
K is an uncharged mono- or bidentate ligand;
q is the number of carbene ligands, where n is at least 1 and the carbene ligands in the complex of the formula I when q>1 may be the same or different;
r is the number of ligands L, where m may be 0 or 1, and the ligands L when r>1 may be the same or different;
is the number of ligands K, where o may be 0 or 1, and the ligands K, when o>1, may be the same or different;
p is the charge of the complex: 0, 1, 2, 3 or 4; preferably 0, 1 or 2, more preferably 0;
W is a monoanionic counterion;
where the sum of q+r+o and the charge p depends on the oxidation state and coordination number of the metal atom used, the charge of the complex and the denticity of the carbene, L and K ligands, and on the charge of the carbene and L ligands, with the condition that n is at least 1.

The present invention therefore further provides an organic light-emitting diode in which the emitter material used in the light-emitting layer is at least one carbene complex of the general formula (II).

Suitable carbene complexes of the formula (II) are known to those skilled in the art and are described, for example, in WO 2005/019373 A2, WO 2006/056418 A2, WO 2005/113704, WO 2007/115970, WO 2007/115981 and WO 2008/000727.

Further suitable carbene complexes which are preferred emitter materials are described in the not pre-published applications having the reference numbers EP 10 187 176.2 and U.S. 61/391,712 and the published applications WO 2011/073149 and WO 12/121936 A1, especially compounds 5, 8, 9, 10, 21, 22, 24, 25, 26, 28, 29, 30 and the compound of the formula

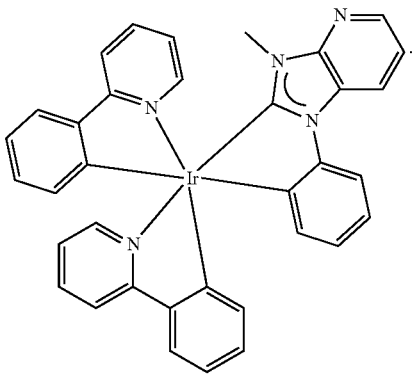

The carbene complexes mentioned in EP 10 187 176.2 and U.S. 61/391,712 and the published application WO 2011/073149 are carbene complexes oft the general formula

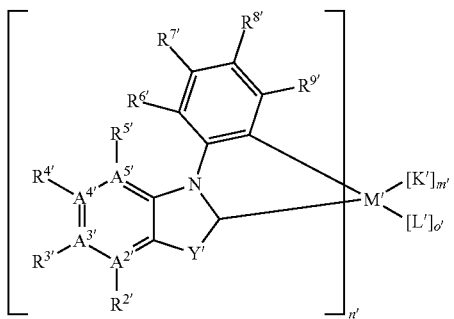

wherein M', n', Y', $A^{2'}$, $A^{3'}$, $A^{4'}$, $A^{5'}$, $R^{1'}$, $R^{2'}$, $R^{3'}$, $R^{4'}$, $R^{5'}$, $R^{6'}$, $R^{7'}$, $R^{8'}$, $R^{9'}$, $R^{10'}$, K', L', m' and o' are defined as follows:

M' is Ir or Pt, n' is an integer selected from 1, 2 or 3,

Y' is $NR^{1'}$, O, S or $C(R^{10'})_2$, $A^{2'}$, $A^{3'}$, $A^{4'}$, $A^{5'}$ are independently of each other N or C, wherein 2 A' are =N-atoms and between two N-atoms in the ring at least one C-atom is present, $R^{1'}$ is a linear or branched alkyl residue having from 1 to 20 carbon atoms, which is optionally interrupted by at least one heteroatom and optionally bears at least one functional group, a cycloalkyl residue having from 3 to 20 carbon atoms, a substituted or unsubstituted aryl residue having from 6 to 30 carbon atoms, a substituted or unsubstituted heteroaryl residue having a total of from 5 to 18 carbon atoms and/or heteroatoms, $R^{2'}$, $R^{3'}$, $R^{4'}$, $R^{5'}$ are, if $A^{2'}$, $A^{3'}$, $A^{4'}$ and/or $A^{5'}$ are N, a free electron pair or, if $A^{2'}$, $A^{3'}$, $A^{4'}$ and/or $A^{5'}$ are C, independently of each other hydrogen, a linear or branched alkyl residue having from 1 to 20 carbon atoms, which is optionally interrupted by at least one heteroatom and optionally bears at least one functional group, a cycloalkyl residue having from 3 to 20 carbon atoms, a substituted or unsubstituted aryl residue having from 6 bis 30 carbon atoms, a substituted or unsubstituted heteroaryl residue having a total of from 5 to 18 carbon atoms and/or heteroatoms, a group having donor or acceptor action, or $R^{3'}$ and $R^{4'}$ form together with $A^{3'}$ and $A^{4'}$ an unsaturated ring having a total of from 5 to 18 carbon atoms and/or heteroatoms, which is optionally interrupted by at least one further heteroatom and optionally substituted, $R^{6'}$, $R^{7'}$, $R^{8'}$, $R^{9'}$ are independently of each other hydrogen, a linear or branched alkyl residue having from 1 to 20 carbon atoms, which is optionally interrupted by at least one heteroatom and optionally bears at least one functional group, a cycloalkyl residue having from 3 to 20 carbon atoms, a cycloheteroalkyl residue having from 3 to 20 carbon atoms, a substituted or unsubstituted aryl residue having from 6 bis 30 carbon atoms, a substituted or unsubstituted heteroaryl residue having a total of from 5 to 18 carbon atoms and/or heteroatoms, a group having donor or acceptor action, or $R^{6'}$ and $R^{7'}$, $R^{7'}$ and $R^{8'}$ or $R^{8'}$ and $R^{9'}$ form together with the C-atoms to which $R^{6'}$, $R^{7'}$, $R^{8'}$ and $R^{9'}$ are linked, an unsaturated ring having a total of from 5 to 18 carbon atoms and/or heteroatoms, which is optionally interrupted by at least one further heteroatom and is optionally substituted, and/or if $A^{5'}$ is C, $R^{5'}$ and $R^{6'}$ together form a bridge comprising a total of from 1 to 30 carbon atoms and/or heteroatoms which is optionally annulated with a substituted or unsubstituted five to eight membered carbon atoms and/or heteroatoms comprising ring, which bridge is saturated or unsaturated, linear or branched, optionally comprises heteroatoms, an aromatic unit, a heteroaromatic unit and/or functional groups, $R^{10'}$ is a linear or branched alkyl residue having from 1 to 20 carbon atoms, which is optionally interrupted by at least one heteroatom and optionally bears at least one functional group, a cycloalkyl residue having from 3 to 20 carbon atoms, a substituted or unsubstituted aryl residue having from 6 to 30 carbon atoms, a substituted or unsubstituted heteroaryl residue having a total of from 5 to 18 carbon atoms and/or heteroatoms, K' is an uncharged mono- or bidentate ligand, L' is a mono- or dianionic ligand, preferably a monoanionic ligand, which may be mono- or bidentate, m' is 0, 1 or 2, and the ligands K', when m is 2, may be the same or different, o' is 0, 1 or 2, and the ligands L', when o is 2, may be the same or different.

One example for a carbene complex mentioned above is a carbene complex of the formula (III)

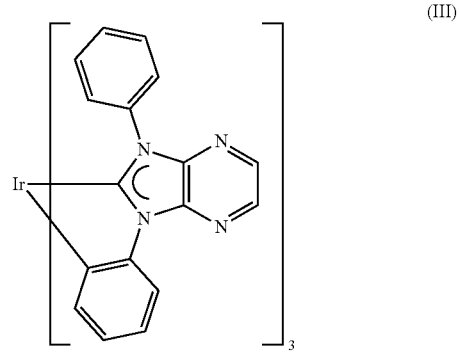

(III)

The light-emitting layer may comprise further components in addition to the emitter material. For example, a fluorescent dye may be present in the light-emitting layer in order to alter the emission color of the emitter material. In addition—in a preferred embodiment—a host (matrix) material can be used. This matrix material may be a polymer, for example poly(N-vinylcarbazole) or polysilane. The matrix material may, however, likewise be a small molecule, for example 4,4'-N,N'-dicarbazolebiphenyl (CDP=CBP) or tertiary aromatic amines, for example TCTA.

In a preferred embodiment, the host (matrix) material is at least one carbene complex. Suitable carbene complexes are mentioned above. An especially suitable carbene complex is Ir(dpbic)$_3$ which has been described above.

In a further preferred embodiment of the present invention, at least one compound of the formula (I) is used as host (matrix) material. This at least one compound of formula (I) can be used together with at least one further host (matrix) material, preferably together with at least one carbene complex, e.g. together with Ir(dpbic)$_3$.

In a further preferred embodiment, the light emitting layer comprises a compound of formula (III) as emitter material together with a compound of formula (I) as host material. The light emitting layer may additionally comprise Ir(dpbic)$_3$ as further host material.

In a preferred embodiment, the light-emitting layer is formed from 2 to 60% by weight, preferably 5 to 55% by weight, more preferably 10 to 50% by weight of at least one of the aforementioned emitter materials, preferably at least one phosphorescence emitter, more preferably at least one carbene emitter, e.g. at least one carbene emitter as described in WO 2011/073149, and 40 to 98% by weight, preferably 45 to 95% by weight, more preferably 50 to 90% by weight of at least one of the aforementioned matrix materials, for example a carbene complex, wherein Ir(dpbic)$_3$ is an example for a suitable carbene complex, or—in a further embodiment—at least one compound of the formula (I) or a combination of at least one compound of the formula (I) and at least one carbene complex, wherein Ir(dpbic)$_3$ is an example for a suitable carbene complex, where the sum total of the emitter material and of the host (matrix) material adds up to 100% by weight. If more than one host (matrix) material is employed, for example a combination of at least one compound of the formula (I) and at least one carbene complex, wherein Ir(dpbic)$_3$ is an example for a suitable carbene complex, the mass ratio of the host materials is in the case of two host materials, wherein the first host material is a compound of formula (I) and the second host material is a host material mentioned before, preferably a carbene complex, for example Ir(dpbic)$_3$, usually 1.5 to 25:1, preferably 2 to 20:1.

In a further embodiment, the compounds of the formula (I) are used as electron/hole/exciton transport material and/or as electron/hole/exciton blocker material, preferably together with carbene complexes as triplet emitters. The compounds of the formula (I) may additionally—as mentioned above—be used as host (matrix) materials (optionally together with a further host material, wherein preferred further host materials and weight ratios are mentioned before) or both as host (matrix) materials (optionally together with a further host material, wherein preferred further host materials and weight ratios are mentioned before) and as hole/exciton blocker materials together with carbene complexes as triplet emitters. In addition, it is possible that at least one compound of the formula (I) is present in a transporting layer for electrons/holes/excitons, a blocking layer for electrons/holes/excitons and/or a electron/hole/exciton injection layer of the OLED, preferably together with carbene complexes as triplet emitters.

Suitable metal complexes for use together with the compounds of the formula (I) as host (matrix) material and/or electron/hole/exciton transport material and/or electron/hole/exciton blocker material and/or electron/hole/exciton injection material in OLEDs are thus, for example, also carbene complexes as described in WO 2005/019373 A2, WO 2006/056418 A2, WO 2005/113704, WO 2007/115970, WO 2007/115981 and WO 2008/000727, as well as in the not pre-published applications having the reference numbers EP 10 187 176.2 and U.S. 61/391,712 and the published application WO 2011/073149. Explicit reference is made here to the disclosure of the WO applications cited, and these disclosures shall be considered to be incorporated into the content of the present application.

If the blocking layer for holes/excitons (4) does not comprise any compounds of the formula (I), the OLED has—if a blocking layer for holes is present—hole blocker materials typically used in OLEDs, such as 2,6-bis(N-carbazolyl)pyridine (mCPy), 2,9-dimethyl-4,7-diphenyl-1,10-phenanthroline (bathocuproin, (BCP)), bis(2-methyl-8-quinolinato)-4-(phenylphenylato)aluminum(III) (BAlq), phenothiazine S,S-dioxide derivatives and 1,3,5-tris(N-phenyl-2-benzylimidazolyl)benzene (TPBI), TPBI also being suitable as electron-conducting material. Further suitable hole blockers and/or electron conductor materials are 2,2',2"-(1,3,5-benzenetriyl)tris(1-phenyl-1H-benzimidazole), 2-(4-biphenylyl)-5-(4-tert-butylphenyl)-1,3,4-oxadiazole, 8-hydroxyquinolinolatolithium, 4-(naphthalen-1-yl)-3,5-diphenyl-4H-1,2,4-triazole, 1,3-bis[2-(2,2'-bipyridin-6-yl)-1,3,4-oxadiazol-5-yl]benzene, 4,7-diphenyl-1,10-phenanthroline, 3-(4-biphenylyl)-4-phenyl-5-tert-butylphenyl-1,2,4-triazole, 6,6'-bis[5-(biphenyl-4-yl)-1,3,4-oxadiazol-2-yl]-2,2'-bipyridyl, 2-phenyl-9,10-di(naphthalen-2-yl)anthracene, 2,7-bis[2-(2,2'-bipyridin-6-yl)-1,3,4-oxadiazol-5-yl]-9,9-dimethylfluorene, 1,3-bis[2-(4-tert-butylphenyl)-1,3,4-oxadiazol-5-yl]benzene, 2-(naphthalen-2-yl)-4,7-diphenyl-1,10-phenanthroline, tris(2,4,6-trimethyl-3-(pyridin-3-yl)phenyl)borane, 2,9-bis(naphthalen-2-yl)-4,7-diphenyl-1,10-phenanthroline, 1-methyl-2-(4-(naphthalen-2-yl)phenyl)-1H-imidazo[4,5-f][1,10]phenanthroline. In a further embodiment, it is possible to use compounds which comprise aromatic or heteroaromatic rings joined via groups comprising carbonyl groups, as disclosed in WO2006/100298, disilyl compounds selected from the group consisting of disilylcarbazoles, disilylbenzofurans, disilylbenzothiophenes, disilylbenzophospholes, disilylbenzothiophene S-oxides and disilylbenzothiophene S,S-dioxides, as specified, for example, in PCT applications WO 2009/003919 and WO 2009/000872, and disilyl compounds as disclosed in WO2008/034758, as a blocking layer for holes/excitons (4) or as matrix materials in the light-emitting layer (3).

In a preferred embodiment, the present invention relates to an inventive OLED comprising the layers (1) anode, (2) hole conductor layer, (3) light-emitting layer, (4) blocking layer for holes/excitons, (5) electron conductor layer and (6) cathode, and optionally further layers, wherein the transporting layer for electrons/holes excitons and/or the blocking layer for electrons/holes/excitons and/or the light-emitting layer comprises at least one compound of the formula (I). In addition, the OLED, in a further preferred embodiment, comprises a hole/exciton injection layer (1a), which is generally arranged between the anode (1) and the hole conductor layer (2). Suitable materials for the hole injection layer are known to those skilled in the art.

Suitable electron conductor materials for layer (5) of the inventive OLEDs comprise metals chelated to oxinoid compounds, such as 2,2',2''-(1,3,5-phenylene)tris[1-phenyl-1H-benzimidazole](TPBI), tris(8-quinolinolato)aluminum ($Alq_3$), compounds based on phenanthroline, such as 2,9-dimethyl-4,7-diphenyl-1,10-phenanthroline (DDPA=BCP) or 4,7-diphenyl-1,10-phenanthroline (DPA), and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ), 8-hydroxyquinolinolatolithium (Liq), 4,7-diphenyl-1,10-phenanthroline (BPhen), bis(2-methyl-8-quinolinolato)-4-(phenylphenolato)aluminum (BAlq), 1,3-bis[2-(2,2'-bipyridin-6-yl)-1,3,4-oxadiazol-5-yl]benzene (Bpy-OXD), 6,6'-bis[5-(biphenyl-4-yl)-1,3,4-oxadiazol-2-yl]-2,2'-bipyridyl (BP-OXD-Bpy), 4-(naphthalen-1-yl)-3,5-diphenyl-4H-1,2,4-triazole (NTAZ), 2,9-bis(naphthalen-2-yl)-4,7-diphenyl-1,10-phenanthroline (NBphen), 2,7-bis[2-(2,2'-bipyridin-6-yl)-1,3,4-oxadiazol-5-yl]-9,9-dimethylfluorene (Bby-FOXD), 1,3-bis[2-(4-tert-butylphenyl)-1,3,4-oxadiazol-5-yl]benzene (OXD-7), tris(2,4,6-trimethyl-3-(pyridin-3-yl)phenyl)borane (3TPYMB), 1-methyl-2-(4-(naphthalen-2-yl)phenyl)-1H-imidazo[4,5-f][1,10]phenanthroline (2-NPIP), 2-phenyl-9,10-di(naphthalen-2-yl)anthracene (PADN), 2-(naphthalen-2-yl)-4,7-diphenyl-1,10-phenanthroline (HN-Bphen).

Further suitable electron conductor materials for layer are mentioned in WO 2012/121936 A2, especially in the tables on pages 57, 58 and 59, i.e. bathocuprine compounds (e.g. BCP, BPhen); metal 8-hydroxyquinolates (e.g. BAlq, $Alq_3$, $Zrq_4$); 5-member ring electron deficient heterocycles such as triazole, oxadiazole, imidazole and benzoimidazole; triphenylene compounds; fluorinated aromatic compounds; phenothiazine-S-oxides; phenothiazine-S,S-dioxides; anthracene-benzoimidazole compounds, aza triphenylene derivatives; anthracene-benzothiazole compounds; metal hydroxybenoquinolates; silole compounds; arylborane compounds; fullerenes (e.g. C60) and triazine complexes.

The layer (5) may serve both to facilitate electron transport and as a buffer layer or barrier layer in order to prevent quenching of the exciton at the interfaces of the layers of the OLED. The layer (5) preferably improves the mobility of the electrons and reduces quenching of the exciton. In a preferred embodiment, BCP is used as the electron conductor material. In principle, it is possible that the electron conductor layer comprises at least one compound of the formula (I) as an electron conductor material.

It is likewise possible to use mixtures of at least two materials in the electron-transporting (electron-conducting) layer, in which case at least one material is electron-conducting. Preferably, in such mixed electron-transporting layers, at least one phenanthroline compound is used. More preferably, in mixed electron-transporting layers, alkali metal hydroxyquinolate complexes, for example Liq, are used in addition to at least one phenanthroline compound. Furthermore, it is possible to use mixtures which lead to electrical n-doping of the electron-transporting layer. n-Doping is achieved by the addition of reducing materials. These mixtures may, for example, be mixtures of the abovementioned electron transport materials with alkali/alkaline earth metals or alkali/alkaline earth metal salts, for example Li, Cs, Ca, Sr, $Cs_2CO_3$, with alkali metal complexes, for example 8-hydroxyquinolinolatolithium (Liq), and with Y, Ce, Sm, Gd, Tb, Er, Tm, Yb, $Li_3N$, $Rb_2CO_3$, dipotassium phthalate, $W(hpp)_4$ from EP 1786050 or with compounds as described in EP1 837 926 B1.

The present invention therefore also relates to an inventive OLED which comprises an electron-transporting layer comprising at least two different materials, at least one material of which should be electron-conducting.

In a preferred embodiment, the present invention relates to an inventive OLED wherein the electron-transporting layer comprises at least one phenanthroline derivative.

In a further preferred embodiment, the invention relates to an inventive OLED wherein the electron-transporting layer comprises at least one phenanthroline derivative and at least one alkali metal hydroxyquinolate complex.

In a further preferred embodiment, the invention relates to an inventive OLED wherein the electron-transporting layer comprises at least one phenanthroline derivative and 8-hydroxyquinolinolatolithium (Liq).

Among the materials mentioned above as hole conductor materials and electron conductor materials, some may fulfil several functions. For example, some of the electron-conducting materials are simultaneously hole-blocking materials when they have a low-lying HOMO. These can be used, for example, in the blocking layer for holes/excitons (4). However, it is likewise possible that the function as a hole/exciton blocker is also adopted by the layer (5), such that the layer (4) can be dispensed with.

The charge transport layers can also be electronically doped in order to improve the transport properties of the materials used, in order firstly to make the layer thicknesses more generous (avoidance of pinholes/short circuits) and in order secondly to minimize the operating voltage of the device. p-Doping is achieved by the addition of oxidizing materials. These mixtures may, for example, be mixtures of the abovementioned hole transport materials with $MoO_2$, $MoO_3$, $WO_x$, $ReO_3$, $V_2O_5$, 7,7,8,8-tetracyanoquinodimethane (TCNQ), 2,3,5,6-tetrafluoro-7,7,8,8-tetracyanoquinodimethane ($F_4$-TCNQ), 2,5-bis(2-hydroxyethoxy)-7,7,8,8-tetracyanoquinodimethane, bis(tetra-n-butylammonium) tetracyanodiphenoquinodimethane, 2,5-dimethyl-7,7,8,8-tetracyanoquinodimethane, tetracyanoethylene, 11,11,12,12-tetracyanonaphtho-2,6-quinodimethane, 2-fluoro-7,7,8,8-tetracyanoquinodimethane, 2,5-difluoro-7,7,8,8-tetracyanoquinodimethane, dicyanomethylene-(1,3,4,5,7,8-hexafluoro-6H-naphthalen-2-ylidene)malononitrile ($F_6$-TNAP), $Mo(tfd)_3$ (from Kahn et al., J. Am. Chem. Soc. 2009, 131 (35), 12530-12531), and with quinone compounds as mentioned in US 2011 0253988.

The electron conductor materials can be doped, for example, with alkali metals, for example $Alq_3$ with lithium. In addition, electron conductors can be doped with salts such as $Cs_2CO_3$. Electronic doping is known to those skilled in the art and is disclosed, for example, in W. Gao, A. Kahn, J. Appl. Phys., vol. 94, No. 1, Jul. 1, 2003 (p-doped organic layers); A. G. Werner, F. Li, K. Harada, M. Pfeiffer, T. Fritz, K. Leo. Appl. Phys. Lett., vol. 82, No. 25, Jun. 23, 2003 and Pfeiffer et al., Organic Electronics 2003, 4, 89-103. For example, the hole conductor layer can be doped a, in addition to a carbene complex, e.g. $Ir(dpbic)_3$, with $MoO_3$ or $WO_3$.

The cathode (6) is an electrode which serves to introduce electrons or negative charge carriers. Suitable materials for the cathode are selected from the group consisting of alkali metals of group Ia, for example Li, Cs, alkaline earth metals of group IIa, for example calcium, barium or magnesium, metals of group IIb of the Periodic Table of the Elements (old IUPAC version), comprising the lanthanides and actinides, for example samarium. In addition, it is also possible to use metals such as aluminum or indium, and combinations of all metals mentioned. In addition, lithium-comprising organometallic compounds or LiF can be applied between the organic layer and the cathode in order to reduce the operating voltage.

The OLED according to the present invention may additionally comprise further layers which are known to those skilled in the art. For example, between the layer (2) and the light-emitting layer (3) may be applied a layer which facilitates the transport of the positive charge and/or matches the band gap of the layers to one another. Alternatively, this further layer may serve as a protective layer. In an analogous manner, additional layers may be present between the light-emitting layer (3) and the layer (4) in order to facilitate the transport of the negative charge and/or to match the band gap between the layers to one another. Alternatively, this layer may serve as a protective layer.

In a preferred embodiment, the inventive OLED, in addition to layers (1) to (6), comprises at least one of the further layers mentioned below:
A hole injection layer between the anode (1) and the hole-transporting layer (2);
a blocking layer for electrons between the hole-transporting layer (2) and the light-emitting layer (3);
an electron injection layer between the electron-transporting layer (5) and the cathode (6).

Materials for a hole injection layer may be selected from copper phthalocyanine, 4,4',4"-tris(N-3-methylphenyl-N-phenylamino)triphenylamine (m-MTDATA), 4,4',4"-tris(N-(2-naphthyl)-N-phenylamino)triphenylamine (2T-NATA), 4,4',4"-tris(N-(1-naphthyl)-N-phenylamino)triphenylamine (1T-NATA), 4,4',4"-tris(N,N-diphenylamino)triphenylamine (NATA), titanium oxide phthalocyanine, 2,3,5,6-tetrafluoro-7,7,8,8-tetracyanoquinodimethane ($F_4$-TCNQ), pyrazino[2,3-f][1,10]phenanthroline-2,3-dicarbonitrile (PPDN), N,N,N',N'-tetrakis(4-methoxyphenyl)benzidine (MeO-TPD), 2,7-bis[N,N-bis(4-methoxyphenyl)amino]-9,9-spirobifluorene (MeO-Spiro-TPD), 2,2'-bis[N,N-bis(4-methoxyphenyl)amino]-9,9-spirobifluorene (2,2'-MeO-Spiro-TPD), N,N'-diphenyl-N,N'-di[4-(N,N-ditolylamino)phenyl]benzidine (NTNPB), N,N'-diphenyl-N,N'-di[4-(N,N-diphenylamino)phenyl]benzidine (NPNPB), N,N'-di(naphthalen-2-yl)-N,N'-diphenylbenzene-1,4-diamine (α-NPP), PEDOT-PSS polymer. In principle, it is possible that the hole injection layer comprises at least one compound of the formula (I), (II) or (III) as a hole injection material.

Further suitable materials for a hole injection layer are mentioned in WO 2012/121936 A2, especially on page 100, i.e. UGH2, Compound C, TAPC, 3TPYMB, TPBi, TCTA, UGH3, Compound D, Compound E, Compound F, Compound G and Compound A mentioned on page 100 in WO 2012/121936 A2.

The material selected for the electron injection layer may, for example, be LiF, CsF, KF or $Cs_2CO_3$. In principle, it is possible that the electron injection layer comprises at least one compound of the formula (I) as an electron injection material.

The person skilled in the art is aware (for example on the basis of electrochemical studies) of how suitable materials have to be selected. Suitable materials for the individual layers are known to those skilled in the art and are disclosed, for example, in WO 00/70655.

In addition, it is possible that some of the layers used in the inventive OLED have been surface-treated in order to increase the efficiency of charge carrier transport. The selection of the materials for each of the layers mentioned is preferably determined by obtaining an OLED with a high efficiency and lifetime.

The inventive OLED can be produced by methods known to those skilled in the art. In general, the inventive OLED is produced by successive vapor deposition of the individual layers onto a suitable substrate. Suitable substrates are, for example, glass, inorganic semiconductors or polymer films. For vapor deposition, it is possible to use customary techniques, such as thermal evaporation, chemical vapor deposition (CVD), physical vapor deposition (PVD) and others. In an alternative process, the organic layers of the OLED can be applied from solutions or dispersions in suitable solvents, employing coating techniques known to those skilled in the art.

In general, the different layers have the following thicknesses: anode (1) 50 to 500 nm, preferably 100 to 200 nm; hole-conducting layer (2) 5 to 100 nm, preferably 20 to 80 nm, light-emitting layer (3) 1 to 100 nm, preferably 10 to 80 nm, blocking layer for holes/excitons (4) 2 to 100 nm, preferably 5 to 50 nm, electron-conducting layer (5) 5 to 100 nm, preferably 20 to 80 nm, cathode (6) 20 to 1000 nm, preferably 30 to 500 nm. The relative position of the recombination zone of holes and electrons in the inventive OLED in relation to the cathode and hence the emission spectrum of the OLED can be influenced, among other factors, by the relative thickness of each layer. This means that the thickness of the electron transport layer should preferably be selected such that the position of the recombination zone is matched to the optical resonator property of the diode and hence to the emission wavelength of the emitter. The ratio of the layer thicknesses of the individual layers in the OLED depends on the materials used. The layer thicknesses of any additional layers used are known to those skilled in the art. It is possible that the electron-conducting layer and/or the hole-conducting layer has/have greater thicknesses than the layer thicknesses specified when they are electrically doped.

Use of the compounds of the formula (I) in at least one layer of the OLED, preferably in the light-emitting layer (preferably as host (matrix) material) and/or in the transporting layer for electrons/holes/excitons and/or in the blocking layer for electrons/holes/excitons and/or in the injection layer for electrons/holes/excitons makes it possible to obtain OLEDs with high efficiency and with low use and operating voltage and with long lifetimes. The compounds of formula (I) used in accordance with the invention conduct holes and electrons, i.e. they are bipolar. This can establish a good charge carrier balance, which can achieve better efficiencies and lifetimes. The efficiency of the OLEDs can additionally be improved by optimizing the other layers of the OLEDs. For example, it is possible to use high-efficiency cathodes such as Ca or Ba, optionally in combination with an intermediate layer of LiF, CsF, KF or $Cs_2CO_3$. Shaped substrates and novel hole-transporting materials which bring about a reduction in the operating voltage or an increase in the quantum efficiency are likewise usable in the inventive OLEDs. Moreover, additional layers may be present in the OLEDs in order to adjust the energy level of the different layers and to facilitate electroluminescence.

The OLEDs may further comprise at least one second light-emitting layer. The overall emission of the OLEDs may be composed of the emission of the at least two light-emitting layers and may also comprise white light.

The OLEDs can be used in all apparatus in which electroluminescence is useful. Suitable devices are preferably selected from stationary and mobile visual display units and illumination units. Stationary visual display units are, for example, visual display units of computers, televisions, visual display units in printers, kitchen appliances and advertising panels, illuminations and information panels. Mobile visual display units are, for example, visual display units in smartphones, cellphones, laptops, digital cameras, MP3 players, vehicles and destination displays on buses and trains. Further devices in which the inventive OLEDs can be used are, for example, keyboards; garments; furniture; wallpaper.

In addition, the compounds of the formula (I) can be used in OLEDs with inverse structure. The compounds of the formula (I) used in accordance with the invention are preferably used in these inverse OLEDs again as hole/exciton blocker materials. The structure of inverse OLEDs and the materials typically used therein are known to those skilled in the art.

In addition, the present invention relates to a device selected from the group consisting of stationary visual display units such as visual display units of computers, televisions, visual display units in printers, kitchen appliances and advertising panels, illuminations, information panels, and mobile visual display units such as visual display units in smartphones, cellphones, laptops, digital cameras, MP3 players, vehicles and destination displays on buses and trains; illumination units; keyboards; garments; furniture; wallpaper comprising at least one inventive organic light-emitting diode or at least one inventive light-emitting layer.

In a further embodiment, the compounds of the formula (I) can be used in white OLEDs, preferably as matrix material in a light-emitting layer or as blocker material.

The examples which follow provide additional illustration of the invention.

EXAMPLES

I Synthesis Examples

I.1 Preparation of the building block 2,8-Dibromo-10,10-diphenyl-phenoxasilane (PXBr)

i) Preparation of 2,2',4,4'-Tetrabromodiphenylether

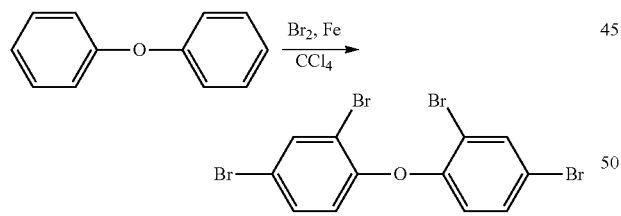

A mixture of diphenyl ether (5.0 g, 29.5 mmol), iron powder (0.1 g, 1.79 mmol) and carbon tetrachloride (50 ml) is heated to 70° C. for 24 hr. To the mixture is added bromine (19.3 g, 120.9 mmol) in carbon tetrachloride (50 ml) keeping the temperature at 75° C. for 1 hour. Then to the reaction mixture is added chloroform (40 ml), then, filtered, and washed with water. The organic layer is separated, and evaporated to dryness. The resulting solid is purified by recrystallization from n-hexane to afford a colorless solid (10.6 g, 74.3%).

$^1$H-NMR (400 MHz, CDCl$_3$): δ 7.79 (d, J=2.28 Hz, 2H), 7.38 (dd, J=2.3 Hz, 2H), 6.71 (d, J=8.7 Hz, 2H), 7.39-7.24 (m, 30H) ppm.

EIMS (m/z)=486 [M$^+$].

ii) Preparation of 2,8-Dibromo-10,10-diphenyl-phenoxasilane (PXBr)

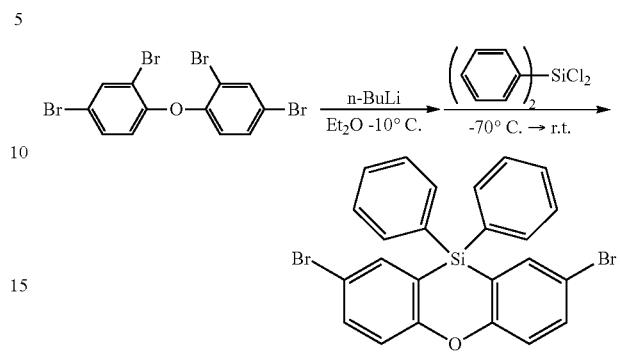

To a round bottom flask is added 2,2',4,4'-tetrabromodiphenylether (3.0 g, 6.176 mmol). After nitrogen flow for 1 hour, dry diethyl ether (30 ml) is added. The resultant mixture is cooled to −10° C. in an ice bath (dry ice/acetone) then n-butyllithium (1.6 M, 8.0 ml) is added dropwise. After stirring for 2 hours at room temperature, the mixture is cooled to −70° C. and dichlorodiphenylsilane (1.6 g, 6.36 mmol) is added dropwise. The resultant mixture is stirred for 19 hours at room temperature, and precipitate is filtered. The organic layer is washed with water, the mixture is separated, and dried over anhydrous MgSO$_4$. Then, the mixture is filtered, and evaporated to dryness, then, purified by chromatography on silica gel (eluent: hexane/toluene=4/1) to afford PXBr (2.1 g, 69.0%)

$^1$H-NMR (400 MHz, CD$_2$Cl$_2$): δ 7.61-7.53 (m, 8H), 7.49-7.38 (m, 6H), 7.18 (d, J=8.7 Hz, 2H) ppm EIMS (m/z)=508 [M$^+$].

I.2 Synthesis of Compound (1)

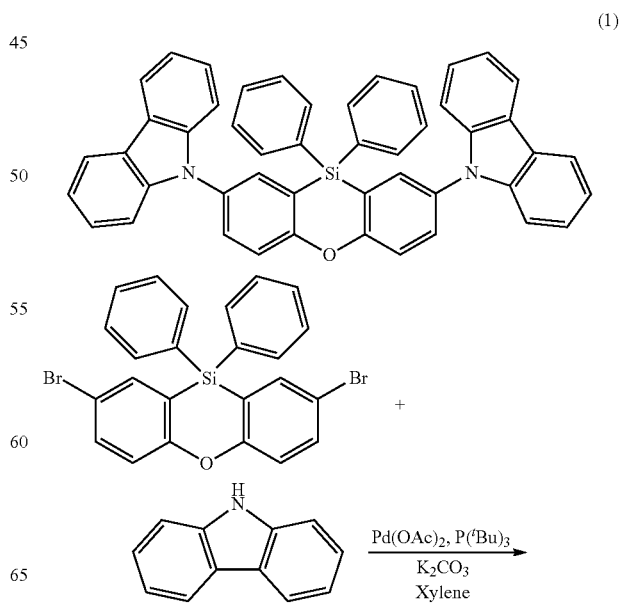

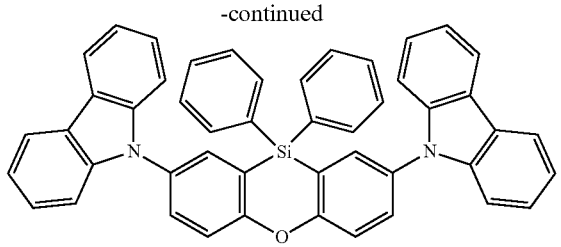

To a round bottom flask is added PXBr (synthesis example I.1) (2.00 g, 3.93 mmol) carbazole (1.38 g, 8.25 mmol), and sodium-tert-butoxide (1.13 g, 11.8 mmol). Dry xylene (80 ml) is added and nitrogen bubbled through the mixture for 1 hour. Then, Pd(OAc)$_2$ (17.6 mg, 79.6 µmol), tritert-butylphosphine (73.8 1, 0.314 mmol) are added and the resultant mixture is vigorously stirred for 5 hours at reflux temperature under N$_2$ flow. The resulting mixture is cooled to room temperature. The precipitate is filtered, and washed with water. The organic layer is separated and dried over anhydrous MgSO$_4$, filtered, and evaporated. The resulting mixture is filtered through silica gel pad (eluent: toluene). The filtrate is evaporated to dryness, poured into hexane to afford a white solid (2.07 g:77.4 g).

$^1$H-NMR: (400 MHz, CD$_2$Cl$_2$): δ 8.14 (d, J=8.0 Hz, 4H), 7.80 (d, J=2.8 Hz, 2H), 7.75 (q, J=8.8 Hz, 2H), 7.67-7.60 (m, 6H), 7.47-7.37 (m, 14H), 7.30-7.26 (m, 4H) ppm.

EIMS (m/z)=681[M$^+$]

Anal, Calcd for C$_{48}$H$_{32}$N$_2$OSi: C, 84.67; H, 4.74; N, 4.11%. Found: C, 84.77; H, 4.55; N, 4.11%.

I.3 Synthesis of Compound (2)

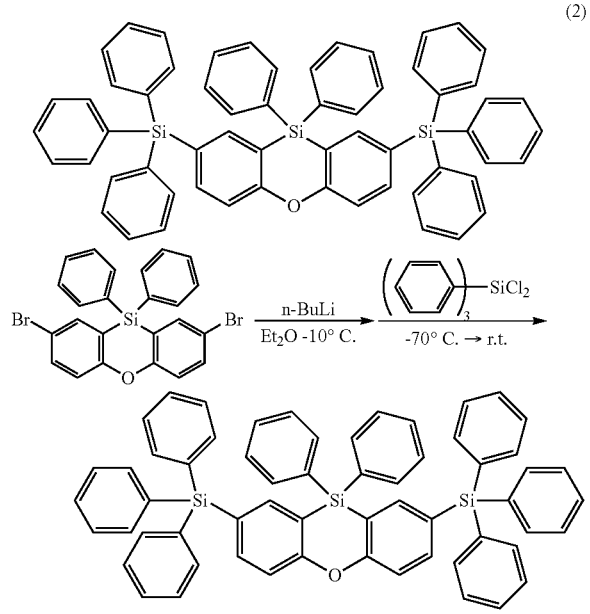

To a round bottom flask is added PXBr (synthesis example I.1) (3.00 g, 5.90 mmol). After nitrogen flow for 1.5 hour, dry tetrahydrofuran (60 ml) is added. The resultant mixture is cooled to −70° C., then n-butyllithium (1.6 M, 11.1 ml) is added dropwise. After stirring for 1 hour at −70° C., ether solution (20 ml) of triphenychlorolsilane (5.21 g, 17.7 mmol) is added dropwise. The resultant mixture is stirred at room temperature. The reaction mixture is evaporated, dissolved in toluene (80 ml) and washed with water. The organic layer is separated and dried over anhydrous MgSO$_4$, filtered, and evaporated to dryness. The resulting solid is purified by recrystallization from toluene to afford a white solid. (2.88 g, 56.3%)

$^1$H-NMR (400 MHz, THF-d$_4$): δ 7.96 (s, 2H), 7.62 (d, J=8.2 Hz, 2H), 7.51 (d, J=8.2 Hz, 12H), 7.39-7.24 (m, 30H) ppm, EIMS (m/z)=868 [M$^+$], Anal, Calcd for C$_{60}$H$_{46}$OSi$_3$: C, 83.09; H, 5.35%. Found: C, 83.04; H, 5.28%.

I.4 Synthesis of Compound (3)

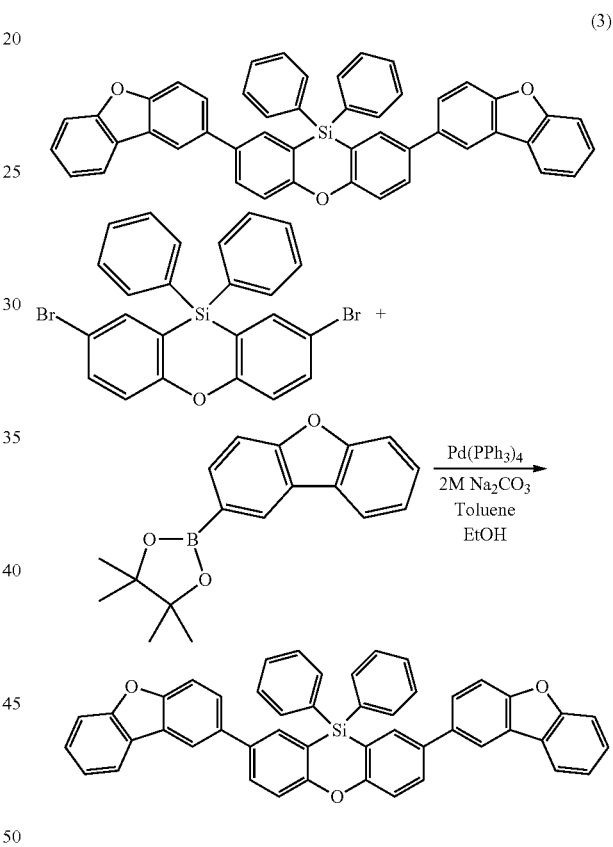

To a round bottom flask is added PXBr (synthesis example I.1) (2.00 g, 3.93 mmol) and dibenzofuran-4-boronic acid (2.43 g, 8.25 mmol). To the mixture are added toluene (40.0 ml), ethanol (20.0 ml) and aqueous Na$_2$CO$_3$ (2.6 M, 11.8 ml) and nitrogen bubbles through the mixture for 1 hour. Then, Pd(PPh)$_4$ (0.23 g, 0.20 mmol) is added and the resultant mixture is vigorously stirred for 12 hours at reflux temperature under N$_2$ flow. The resulting mixture is cooled to room temperature. The precipitate is filtered, and dissolved in reflux toluene (200 ml), filtered through a silica-gel pad. The clear filtrate is evaporated to dryness. The resulting white solid is further purified by recrystallization from toluene (1.45 g, 54%).

1H-NMR (400 MHz, CD2Cl2): δ 8.12 (d, J=2.0 Hz, 2H), 8.01 (d, J=7.6 Hz, 2H), 7.86-7.81 (m, 4H), 7.71-7.56 (m, 10H), 7.49-7.34 (m, 12H) ppm.

EIMS (m/z)=683[M$^+$]

Anal, Calcd for $C_{48}H_{32}N_2OSi$: C, 84.43; H, 4.43%. Found: C, 84.37; H, 4.21%.
I.5 Synthesis of Compounds (4), (5) and (6)
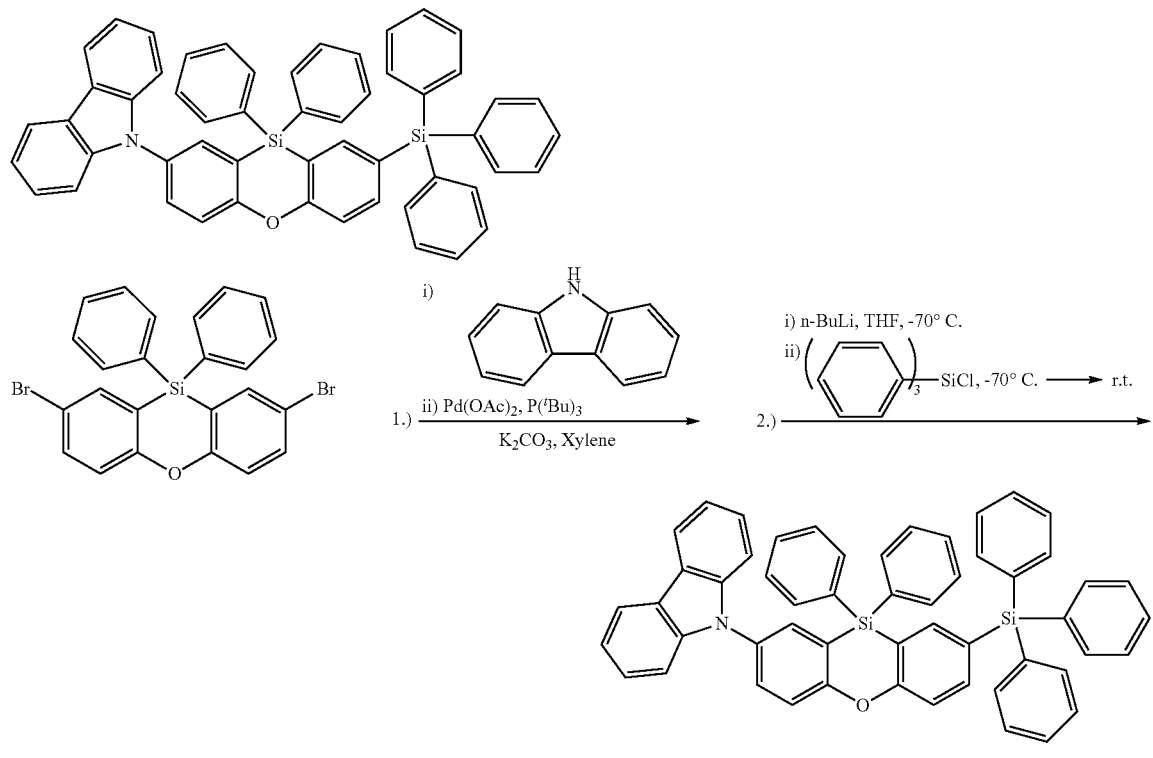
(4)
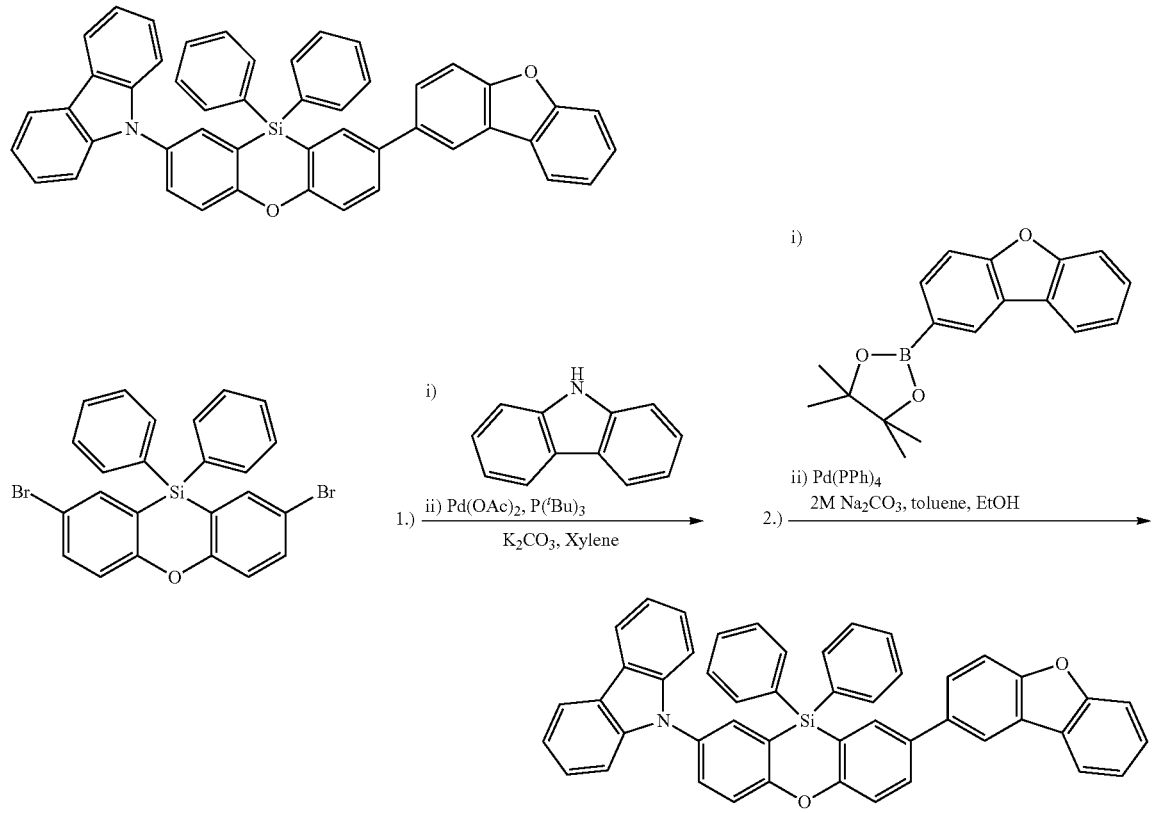
(5)

-continued

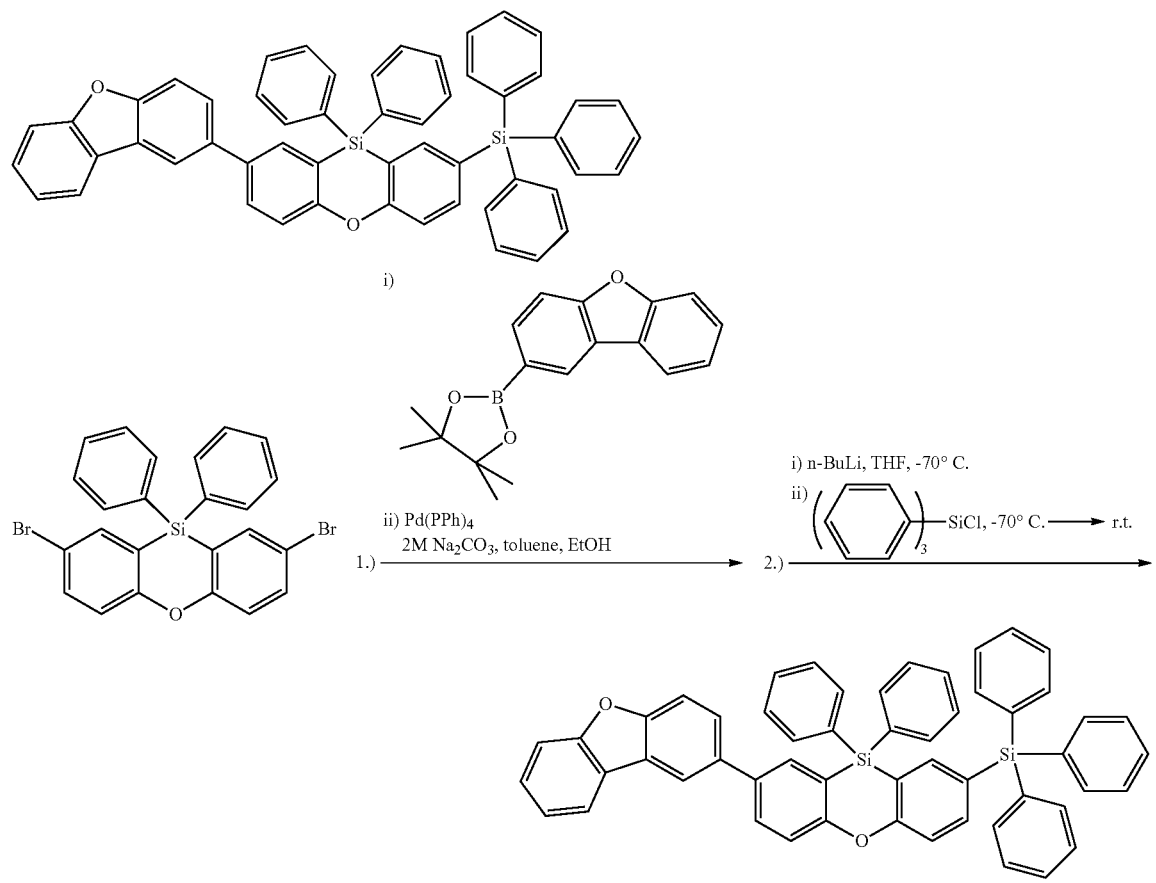

(6)

Compounds (4), (5) and (6) are prepared in analogy to compounds (1), (2) and (3), whereby the correct stoichiometry is to be applied.

I.6 Synthesis of Compound (V7)

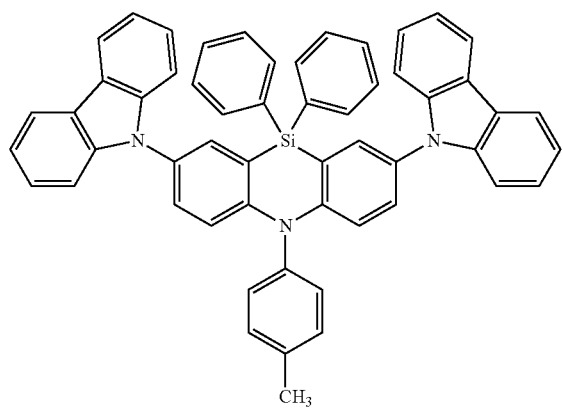

(V7)

Compound (V7) is disclosed in JP2006083167 (CZNTPH).

II Diode Examples

II.1 Production of an OLED Comprising Compound (1) as Host Material and Hole Blocker Material (OLED (1))

The ITO substrate used as the anode is first cleaned with commercial detergents for LCD production (Deconex® 20NS and 25ORGAN-ACID® neutralizing agent) and then in an acetone/isopropanol mixture in an ultrasound bath. To eliminate possible organic residues, the substrate is exposed to a continuous ozone flow in an ozone oven for a further 25 minutes. This treatment also improves the hole injection properties of the ITO. Next, the AJ20-1000 hole injection layer from Plexcore is spun on from solution (~40 nm).

Thereafter, the organic materials specified below are applied to the cleaned substrate by vapor deposition at a rate of approx. 0.5-5 nm/min at about $10^{-8}$ mbar. The hole conductor and exciton blocker applied to the substrate is Ir(dpbic)$_3$ (V1) (DPBIC) with a thickness of 35 nm doped with MoO$_3$ (~50% by weight) to improve the conductivity.

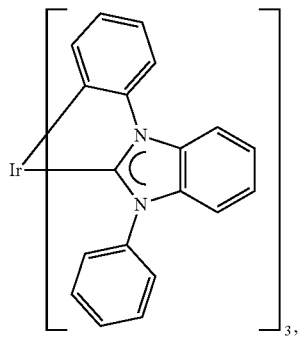

(VI)

disclosed, for example, in WO2005/019373

Subsequently, Ir(dpbic)₃ (V1) is applied by vapor deposition in a thickness of 5 nm.

Subsequently, a mixture of Emitter (E1) (30% by weight), Ir(dpbic)₃ (V1) (host H₁) (15% by weight) and compound (1) (synthesis example I.2) (host H₂) (55% by weight) are applied by vapor deposition in a thickness of 40 nm the former compound functioning as an emitter material, the two latter as matrix materials. The weight ratios of E1, H1 and H2 are given below.

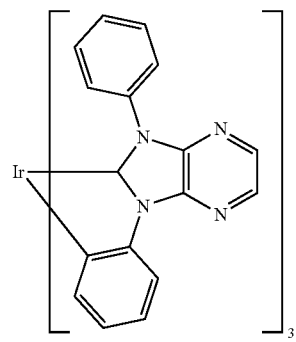

(E1)

disclosed in WO 2011/073149

Subsequently, the compound (1) is applied by vapor deposition with a thickness of 5 nm as an exciton and hole blocker.

Next, as an electron transporter, a mixture of 50 wt. % (V2) and 50 wt. % Liq in a thickness of 25 nm, a 0.7 nm-thick KF layer and finally a 100 nm-thick Al electrode are applied by vapor deposition. All components are bonded to a glass cover in an inert nitrogen atmosphere.

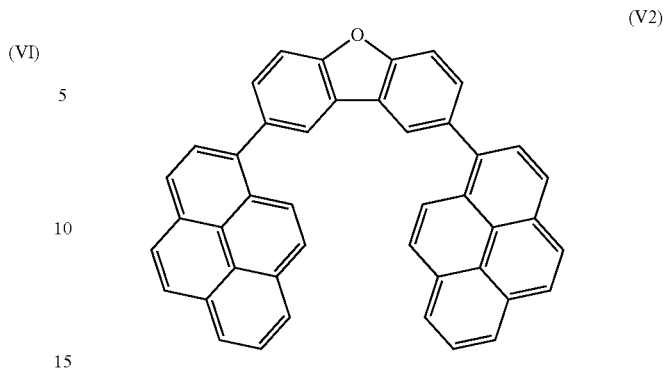

(V2)

disclosed in WO 2006/128800 A1

II.2 Production of an OLED Comprising Compound (2) as Host Material and Hole Blocker Material (OLED (2))

As example II.1, except that the host material and the hole blocker material used is compound (2) according to synthesis example I.3 instead of compound (1).

II.3 Production of an OLED Comprising Compound (3) as Host Material and Hole Blocker Material (OLED (3))

As example II.1, except that the host material and the hole blocker material used is compound (3) according to synthesis example I.4 instead of compound (1).

II.4 Production of an OLED Comprising Comparative Compound (V7) as Host Material and Hole Blocker Material (OLED (V7))

As example II.1, except that the host material and the hole blocker material used is compound (V7) according to synthesis example I.5 instead of compound (1).

Results

To characterize the OLEDs of examples II.1, II.2 and II.3 and the OLED of comparative example II.4, electroluminescence spectra are recorded at different currents and voltages. In addition, the current-voltage characteristic is measured in combination with the emitted light output. The light output can be converted to photometric parameters by calibration with a photometer. The data are shown in table 1.

II.5 Production of an OLEDs Comprising Compounds (4), (5) and (6) as Host Material and Hole Blocker Material (OLEDs (4), (5) and (6))

As example II.1, except that the host material and the hole blocker material used is compound (4), (5) or (6), respectively according to synthesis example I.5 instead of compound (1).

The OLEDs (4), (5) and (6) obtained emit blue light.

TABLE 1

| OLED Example (host and hole blocker) | CIE-x[1] absolute values | CIE-y[2] absolute values | Voltage 300 nits normalized values[3] | EQE[4] 300 nits normalized values[3] | LD[5] 300 nits normalized values[3] |
|---|---|---|---|---|---|
| OLED II.1 (1) | 0.177 | 0.347 | 0.798 | 7.683 | 3.635 |
| OLED II.2 (2) | 0.188 | 0.37 | 0.691 | 9.025 | 34.594 |
| OLED II.3 (3) | 0.188 | 0.381 | 0.716 | 7.935 | 4.421 |
| OLED II.4 (V7) | 0.18 | 0.329 | 1.000 | 1.000 | 1.000 |

[1] CIE (International Commission on Illumination) color coordinate: x-coordinate
[2] CIE (International Commission on Illumination) color coordinate: y-coordinate
[3] Normalized values: Normalized relative to the values of comparative OLED II.4 (host and hole blocker material: (V7)) - the values of the comparative OLED II.4 (host and hole blocker material: (V7)) are set to 1.000
[4] EQE: external quantum efficiency
[5] LD: lifetime

CONCLUSION

The performance of the inventive OLEDs (1) to (3) is clearly superior compared with the performance of the comparative OLED (V7). The only difference between the inventive OLEDs and the comparative OLED is the material employed as host in the light emitting layer and as exciton and hole blocker, which is according to the present invention a phenoxasiline compound and according to the comparative example a phenazasiline compound. The superiority of the inventive phenoxasilines over phenazasilines is especially evident in the following OLED properties:
i) Voltage: the OLEDs of the present invention comprising the phenoxasilines according to the present invention perform at significantly lower voltage than OLEDs comprising phenazasilines;
ii) External quantum efficiency (EQE): the OLEDs of the present invention comprising the phenoxasilines according to the present invention show a significantly higher EQE than OLEDs comprising phenazasilines;
iii) Lifetime (LD): the OLEDs of the present invention comprising the phenoxasilines according to the present invention show a significantly longer lifetime than OLEDs comprising phenazasilines; this is especially clear from the direct comparison of OLED II.2 (host and hole blocker material: (2)) and OLED II.4 (host and hole-blocker material (V7)), wherein the substituents of the phenoxasiline (according to the present invention; (2)) and the phenazasiline (comparative example; (V7)) are identical.

The invention claimed is:
1. An organic electronic device comprising at least one compound of the formula (I):

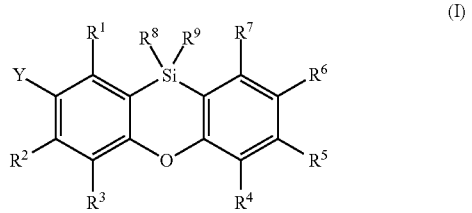

in which
$R^1$, $R^2$, $R^3$, $R^4$, $R^5$, $R^6$ and $R^7$
are each independently hydrogen, $C_1$-$C_{20}$-alkyl, $C_3$-$C_{20}$-cycloalkyl, heterocycloalkyl having 3 to 20 ring atoms, $C_6$-$C_{30}$-aryl, heteroaryl having 5 to 30 ring atoms or a substituent with donor or acceptor action selected from the group consisting of $C_1$-$C_{20}$-alkoxy, $C_6$-$C_{30}$-aryloxy, $C_1$-$C_{20}$-alkylthio, $C_6$-$C_{30}$-arylthio, $SiR^{10}R^{11}R^{12}$, halogen radicals, halogenated $C_1$-$C_{20}$-alkyl radicals, carbonyl (—CO($R^1$)), carbonylthio (—C=O($SR^{10}$)), carbonyloxy (—C=O($OR^{10}$)), oxycarbonyl (—OC=O($R^{10}$)), thiocarbonyl (—SC=O($R^{10}$)), amino (—$NR^{10}R^{11}$), OH, pseudohalogen radicals, amido (—C=O($NR^{10}R^{11}$)), —$NR^{10}$C=O($R^{11}$), phosphonate (—P(O)($OR^{10}$)$_2$), phosphate (—OP(O)($OR^{10}$)$_2$), phosphine (—$PR^{10}R^{11}$), phosphine oxide (—P(O)$R^{10}{}_2$), sulfate (—OS(O)$_2$$OR^{10}$), sulfoxide (—S(O)$R^{10}$), sulfonate (—S(O)$_2$$OR^{10}$), sulfonyl (—S(O)$_2$$R^{10}$), sulfonamide (—S(O)$_2$$NR^{10}R^{11}$), NO$_2$, boronic esters (—OB($OR^{10}$)$_2$), imino (—C=$NR^{10}$), borane radicals, stannane radicals, hydrazine radicals, hydrazone radicals, oxime radicals, nitroso groups, diazo groups, vinyl groups, sulfoximines, alanes, germanes, boroxines and borazines;
or two adjacent $R^1$, $R^2$, $R^3$, $R^4$, $R^5$, $R^6$ or $R^7$ radicals, in each case together with the carbon atoms to which they are bonded, form a ring having a total of 3 to 12 atoms, where the ring may be saturated or mono- or polyunsaturated and, as well as carbon atoms, may have one or more heteroatoms selected from N, O and P, where the ring may be unsubstituted or mono- or polysubstituted and/or may be fused to further 3- to 12-membered rings;
$R^8$ and $R^9$
are each independently $C_1$-$C_{20}$-alkyl, $C_3$-$C_{20}$-cycloalkyl, heterocycloalkyl having 3 to 20 ring atoms, $C_6$-$C_{30}$-aryl or heteroaryl having 5 to 30 ring atoms;
$R^{10}$, $R^{11}$, $R^{12}$
are each independently $C_1$-$C_{20}$-alkyl, $C_3$-$C_{20}$-cycloalkyl, heterocycloalkyl having 3 to 20 ring atoms, $C_6$-$C_{30}$-aryl, heteroaryl having 5 to 30 ring atoms, —O—Si($C_1$-$C_{20}$-alkyl)$_3$, —O—Si($C_6$-$C_{30}$-aryl)$_3$, $C_1$-$C_{20}$-alkoxy or $C_6$-$C_{30}$-aryloxy;
or two adjacent $R^{10}$ and $R^{11}$, $R^{10}$ and $R^{12}$ or $R^{11}$ and $R^{12}$ radicals, together with the atom to which they are bonded, form a ring having a total of 3 to 12 atoms, where the ring may be saturated or mono- or polyunsaturated and, as well as the atom to which the $R^{10}$, $R^{11}$ or $R^{12}$ radicals are bonded, may have exclusively carbon atoms or one or more further heteroatoms selected from N, O and P, where the ring may be unsubstituted or mono- or polysubstituted and/or may be fused to further 3- to 12-membered rings;
Y is $C_3$-$C_{20}$-cycloalkyl, heterocycloalkyl having 3 to 20 ring atoms, $C_6$-$C_{30}$-aryl, heteroaryl having 5 to 30 ring atoms or a substituent with donor or acceptor action selected from the group consisting of $C_1$-$C_{20}$-alkoxy, $C_6$-$C_{30}$-aryloxy, $C_1$-$C_{20}$-alkylthio, $C_6$-$C_{30}$-arylthio, SiR$^{10}$R$^{11}$R$^{12}$, halogen radicals, halogenated C$_1$-C$_{20}$-alkyl radicals, carbonyl (—CO(R$^{10}$)), carbonylthio (—C=O(SR$^{10}$)), carbonyloxy (—C=O(OR$^{10}$)), oxycarbonyl (—OC=O(R$^{10}$)), thiocarbonyl (—SC=O(R$^{10}$)), amino (—NR$^{10}$R$^{11}$), OH, pseudohalogen radicals, amido (—C=O(NR$^{10}$R$^{11}$)), —NR$^{10}$C=O(R$^{11}$), phosphonate (—P(O)(OR$^{10}$)$_2$), phosphate (—OP(O)(OR$^{10}$)$_2$), phosphine (—PR$^{10}$R$^{11}$), phosphine oxide (—P(O)R$^{11}$$_2$), sulfate (—OS(O$_2$)OR$^{10}$), sulfoxide (—S(O)R$^{10}$), sulfonate (—S(O)$_2$OR$^{10}$), sulfonyl (—S(O)$_2$R$^{10}$), sulfonamide (—S(O)$_2$NR$^{10}$R$^{11}$), NO$_2$, boronic esters (—OB(OR$^{10}$)$_2$), imino (—C=NR$^{10}$), borane radicals, stannane radicals, hydrazine radicals, hydrazone radicals, oxime radicals, nitroso groups, diazo groups, vinyl groups, sulfoximines, alanes, germanes, boroxines and borazines.

2. The organic electronic device according to claim 1, wherein
Y is heteroaryl having 5 to 30 ring atoms selected from the group consisting of pyrrolyl, furanyl, thienyl, and benzoanellated ring systems thereof and
R$^{10}$, R$^{11}$ and R$^{12}$
are each independently C$_6$-C$_{30}$-aryl.

3. The organic electronic device according to claim 1, wherein
Y is selected from the group consisting of

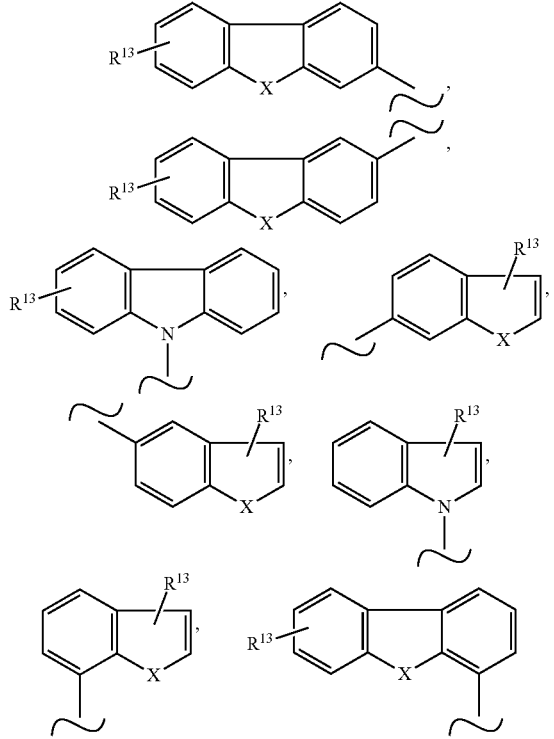

and SiPh$_3$,
wherein
X is NR$^{10}$, O or S,
R$^{10}$ is C$_1$-C$_{20}$-alkyl, C$_3$-C$_{20}$-cycloalkyl, heterocycloalkyl having 3 to 20 ring atoms, C$_6$-C$_{30}$-aryl, heteroaryl having 5 to 30 ring atoms, —O—Si(C$_1$-C$_{20}$-alkyl)$_3$, —O—Si(C$_6$-C$_{30}$-aryl)$_3$, C$_1$-C$_{20}$-alkoxy or C$_6$-C$_{30}$-aryloxy; and
R$^{13}$ is H or phenoxasilinyl of formula (I'),

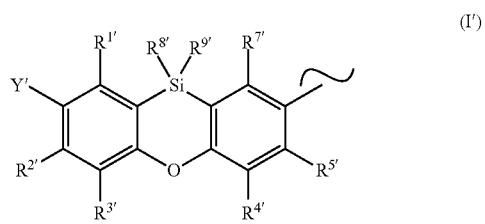

wherein the substituents Y', R$^{2'}$, R$^{3'}$, R$^{4'}$, R$^{5'}$, R$^{7'}$, R$^{8'}$ and R$^{9'}$ have independently the same meanings as the substituents Y, R$^2$, R$^3$, R$^4$, R$^5$, R$^7$, R$^8$ and R$^9$ in the phenoxasiline derivatives of formula (I),
and the symbol ~ means that there is a binding site at the position marked with ~.

4. The organic electronic device according to claim 1, wherein
R$^8$ and R$^9$
are each independently C$_6$-C$_{30}$-aryl or heteroaryl having 5 to 30 ring atoms.

5. The organic electronic device according to claim 1, wherein
R$^8$ and R$^9$ are identical.

6. The organic electronic device according to claim 1, wherein R$^1$, R$^2$, R$^3$, R$^4$, R$^5$, and R$^7$ are each hydrogen and R$^6$ is hydrogen or heteroaryl having 5 to 30 ring atoms selected from the group consisting of pyrrolyl, furanyl, thienyl, and benzoanellated ring systems thereof or SiR$^{10}$R$^{11}$R$^{12}$; or
R$^1$, R$^2$; R$^5$, and R$^7$ are each hydrogen and R$^3$ and R$^4$ are each independently C$_1$-C$_{20}$-alkyl, C$_3$-C$_{20}$-cycloalkyl, heterocycloalkyl having 3 to 20 ring atoms, C$_6$-C$_{30}$-aryl, heteroaryl having 5 to 30 ring atoms, methoxy, phenyloxy, halogenated C$_1$-C$_4$-alkyl, halogen, CN, SiR$^{10}$R$^{11}$R$^{12}$, P(O)Ph$_2$ or diphenylamino and R$^6$ is hydrogen or heteroaryl having 5 to 30 ring atoms selected from the group consisting of pyrrolyl, furanyl, thienyl, and benzoanellated ring systems thereof or SiR$^{10}$R$^{11}$R$^{12}$.

7. The organic electronic device according to claim 6, wherein the compound of formula (I) is selected from the compounds of formulae (Ia), (Ib), (Ic) and (Id)

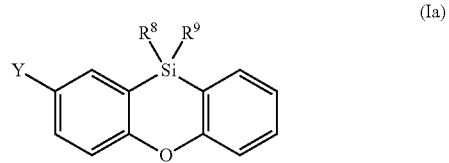

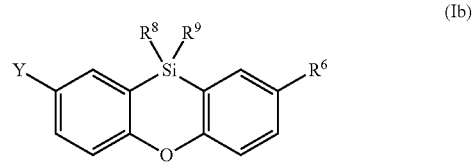

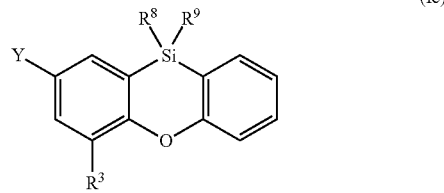

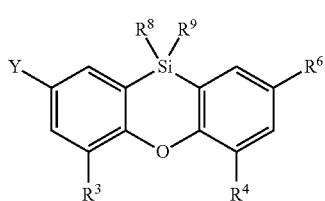

(Id)

wherein
Y and $R^6$
are each independently heteroaryl having 5 to 30 ring atoms selected from the group consisting of pyrrolyl, furanyl, thienyl, and benzoanellated ring systems thereof or $SiR^{10}R^{11}R^{12}$;
$R^3$ and $R^4$
are each independently $C_1$-$C_{20}$-alkyl, $C_3$-$C_{20}$-cycloalkyl, heterocycloalkyl having 3 to 20 ring atoms, $C_6$-$C_{30}$-aryl, heteroaryl having 5 to 30 ring atoms, methoxy, phenyloxy, halogenated $C_1$-$C_4$-alkyl, or halogen;
$R^{10}$, $R^{11}$ and $R^{12}$
are each independently $C_6$-$C_{30}$-aryl;
and
$R^8$ and $R^9$
are each independently $C_6$-$C_{30}$-aryl or heteroaryl having 5 to 30 ring atoms.

8. The organic electronic device according to claim 1, wherein
$R^1$, $R^2$, $R^3$, $R^4$, $R^5$, and $R^7$ are hydrogen, and
$R^6$ is heteroaryl having 5 to 30 ring atoms selected from the group consisting of pyrrolyl, furanyl, thienyl, and benzoanellated ring systems thereof or $SiR^{10}R^{11}R^{12}$, and
$R^{10}$, $R^{11}$ and $R^{12}$
are each independently $C_6$-$C_{30}$-aryl.

9. The organic electronic device according to claim 1, which is an OLED.

10. The OLED according to claim 9 comprising an anode An and a cathode Ka and a light-emitting layer E arranged between the anode An and the cathode Ka, and optionally at least one further layer selected from the group consisting of at least one blocking layer for holes/excitons, at least one blocking layer for electrons/excitons, at least one hole injection layer, at least one hole conductor layer, at least one electron injection layer and at least one electron conductor layer, wherein the at least one compound of the formula (I) is present in the light-emitting layer E and/or when present, in at least one of the further layers.

11. A device selected from the group consisting of stationary visual
display units; mobile visual display units; illumination units; keyboards; garments;
furniture and wallpaper comprising at least one OLED as claimed in claim 9.

12. The organic electronic device according to claim 1, wherein the compound of formula (I) is employed as host material, electron/exciton transport material, hole/exciton transport material, hole/exciton blocker material, electron/exciton blocker material, hole/exciton injection material and/or electron/exciton injection material.

13. A light-emitting layer, electron/exciton transport layer, hole/exciton transport layer, hole/exciton blocking layer, electron/exciton blocking layer, hole/exciton injection layer and/or electron/exciton injection layer comprising at least one compound of formula (I)

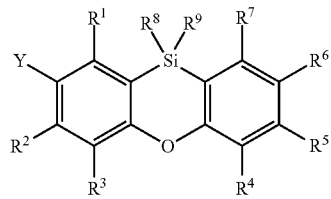

(I)

in which
$R^1$, $R^2$, $R^3$, $R^4$, $R^5$, $R^6$ and $R^7$
are each independently hydrogen, $C_1$-$C_{20}$-alkyl, $C_3$-$C_{20}$-cycloalkyl, heterocycloalkyl having 3 to 20 ring atoms, $C_6$-$C_{30}$-aryl, heteroaryl having 5 to 30 ring atoms or a substituent with donor or acceptor action selected from the group consisting of $C_1$-$C_{20}$-alkoxy, $C_6$-$C_{30}$-aryloxy, $C_1$-$C_{20}$-alkylthio, $C_6$-$C_{30}$-arylthio, $Sir^{10}R^{11}R^{12}$, halogen radicals, halogenated $C_1$-$C_{20}$-alkyl radicals, carbonyl))(—CO($R^{10}$)), carbonylthio))(—C=O($SR^{10}$)), carbonyloxy))(—C=O($OR^{10}$)), oxycarbonyl))(—OC=O($R^{10}$)), thiocarbonyl))(—SC=O($R^{10}$)), amino (—$NR^{10}R^{11}$), OH, pseudohalogen radicals, amido (—C=O($NR^{10}R^{11}$)), —$NR^{10}$C=O($R^{11}$), phosphonate (—P(O)($OR^{10}$), phosphate)(—OP(O)($OR^{10}$)$_2$), phosphine (—$PR^{10}R^{11}$), phosphine oxide (—P(O)($R^{10}$)$_2$), sulfate)(—OS(O)$_2$$OR^{10}$), sulfoxide)(—S(O)$R^{10}$), sulfonate)(—S(O)$_2$$OR^{10}$), sulfonyl) (—S(O)$_2$$R^{10}$), sulfonamide (—S(O)$_2$$NR^{10}R^{11}$), $NO_2$, boronic esters)(—OB($OR^{10}$)$_2$), imino (—C=$NR^{10}$), borane radicals, stannane radicals, hydrazine radicals, hydrazone radicals, oxime radicals, nitroso groups, diazo groups, vinyl groups, sulfoximines, alanes, germanes, boroxines and borazines;

or two adjacent $R^1$, $R^2$, $R^3$, $R^4$, $R^5$, $R^6$ or $R^7$ radicals, in each case together with the carbon atoms to which they are bonded, form a ring having a total of 3 to 12 atoms, where the ring may be saturated or mono- or polyunsaturated and, as well as carbon atoms, may have one or more heteroatoms selected from N, O and P, where the ring may be unsubstituted or mono- or polysubstituted and/or may be fused to further 3- to 12-membered rings;
$R^8$ and $R^9$
are each independently $C_1$-$C_{20}$-alkyl, $C_1$-$C_{20}$-cycloalkyl, heterocycloalkyl having 3 to 20 ring atoms, $C_6$-$C_{30}$-aryl or heteroaryl having 5 to 30 ring atoms;
$R^{10}$, $R^{11}$, $R^{12}$
are each independently $C_1$-$C_{20}$-alkyl, $C_1$-$C_{20}$-cycloalkyl, heterocycloalkyl having 3 to 20 ring atoms, $C_6$-$C_{30}$-aryl, heteroaryl having 5 to 30 ring atoms, —O-Si($C_1$-$C_{20}$-alkyl)$_3$, —O—Si($C_6$-$C_{30}$-aryl)$_3$, $C_1$-$C_{20}$-alkoxy or $C_6$-$C_{30}$-aryloxy;
or two adjacent $R^{10}$ and $R^{11}$, $R^{10}$ and $R^{12}$ or $R^{11}$ and $R^{12}$ radicals, together with the atom to which they are bonded, form a ring having a total of 3 to 12 atoms, where the ring may be saturated or mono- or polyunsaturated and, as well as the atom to which the $R^{10}$, $R^{11}$ or $R^{12}$ radicals are bonded, may have exclusively carbon atoms or one or more further heteroatoms selected from N, O and P, where the ring may be unsubstituted or mono- or polysubstituted and/or may be fused to further 3- to 12-membered rings;
Y is $C_3$-$C_{20}$-cycloalkyl, heterocycloalkyl having 3 to 20 ring atoms, $C_6$-$C_{30}$-aryl, heteroaryl having 5 to 30 ring atoms or a substituent with donor or acceptor action selected from the group consisting of $C_1$-$C_{20}$-alkoxy, $C_6$-$C_{30}$-araloxy, $C_1$-$C_{20}$-alkylthio, $C_6$-$C_{30}$-arylthio, $SiR^{10}R^{11}R^{12}$halogen radicals, halogenated $C_1$-$C_{20}$-alkyl radicals, carbonyl))(—$CO(R^{10})$), carbonylthio))(—$C{=}O(SR^{10})$), carbonyloxy))(—$C{=}O(OR^{10})$), oxycarbonyl))(—$OC{=}O(R^{10})$), thiocarbonyl))(—$SC{=}O(R^{10})$), amino (—$NR^{10}R^{11}$), OH, pseudohalogen radicals, amido (—$C{=}O(NR^{10}R^{11})$), —$NR^{10}C{=}O(R^{11})$, phosphonate)(—$P(O)(OR^{10})_2$), phosphate (—$OP(O)(OR^{10})_2$), phosphine (—$PR^{10}R^{11}$), phosphine oxide)(—$P(O)(R^{10})_2$), sulfate (—$OS(O_2)OR^{10}$), sulfoxide)(—$S(O)R^{10}$), sulfonate)-(—$S(O)_2OR^{10}$), sulfonyl)(—$S(O)_2R^{10}$), sulfonamide (—$S(O),NR^{10}R^{11}$), $NO_2$, boronic esters)(—$OB(OR^{10})_2$), imino)(—$C{=}NR^{10}$), borane radicals, stannane radicals, hydrazine radicals, hydrazone radicals, oxime radicals, nitroso groups, diazo groups, vinyl groups, sulfoximines, alanes, germanes, boroxines and borazines.

\* \* \* \* \*